US008313898B2

(12) United States Patent
Fang et al.

(10) Patent No.: US 8,313,898 B2
(45) Date of Patent: Nov. 20, 2012

(54) DUAL-TARGET BIOSENSOR CELL ASSAYS

(75) Inventors: Ye Fang, Painted Post, NY (US);
Elizabeth Tran, Painted Post, NY (US);
David H. Randle, Corning, NY (US);
Anthony Glenn Frutos, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 575 days.

(21) Appl. No.: 12/388,685

(22) Filed: Feb. 19, 2009

(65) Prior Publication Data
US 2009/0226931 A1 Sep. 10, 2009

Related U.S. Application Data

(60) Provisional application No. 61/068,266, filed on Mar. 5, 2008.

(51) Int. Cl.
C12Q 1/68 (2006.01)
(52) U.S. Cl. .............................. 435/6; 435/325; 435/375
(58) Field of Classification Search ....................... 435/6
See application file for complete search history.

(56) References Cited

U.S. PATENT DOCUMENTS

| 4,815,843 | A | 3/1989 | Tiefenthaler et al. | 356/128 |
|---|---|---|---|---|
| 5,305,074 | A | 4/1994 | Feldman | 356/345 |
| 5,738,825 | A | 4/1998 | Rudigier et al. | 422/82.11 |
| 6,233,471 | B1 | 5/2001 | Berner et al. | 600/345 |
| 6,707,561 | B1 | 3/2004 | Budach et al. | 356/521 |
| 6,727,071 | B1 | 4/2004 | Dunlay et al. | 435/7.21 |
| 6,867,869 | B2 | 3/2005 | Budach et al. | 356/521 |
| 6,870,630 | B2 | 3/2005 | Budach et al. | 356/521 |
| 6,893,705 | B2 | 5/2005 | Thomas et al. | 428/141 |
| 6,985,664 | B2 | 1/2006 | Caracci et al. | 385/130 |
| 7,064,844 | B2 | 6/2006 | Budach et al. | 356/521 |
| 7,105,347 | B2 | 9/2006 | Fang et al. | 435/455 |
| 7,264,973 | B2 | 9/2007 | Lin et al. | 436/518 |
| 7,286,221 | B2 | 10/2007 | Caracci et al. | 356/300 |
| 7,627,201 | B2 | 12/2009 | Tiefenthaler | 385/12 |
| 2002/0127565 | A1 | 9/2002 | Cunningham et al. | 435/6 |
| 2002/0168295 | A1 | 11/2002 | Cunningham et al. | 422/82.05 |
| 2003/0017580 | A1 | 1/2003 | Cunningham et al. | 435/287.2 |
| 2003/0017581 | A1 | 1/2003 | Li et al. | 435/287.2 |
| 2003/0026891 | A1 | 2/2003 | Qiu et al. | 427/58 |
| 2003/0027327 | A1 | 2/2003 | Cunningham et al. | 435/287.2 |
| 2003/0027328 | A1 | 2/2003 | Cunningham et al. | 435/287.2 |
| 2003/0032039 | A1 | 2/2003 | Cunningham et al. | 435/6 |
| 2003/0059855 | A1 | 3/2003 | Cunningham et al. | 435/7.9 |
| 2003/0068657 | A1 | 4/2003 | Lin et al. | 435/7.9 |
| 2003/0077660 | A1 | 4/2003 | Pien et al. | 435/7.1 |
| 2003/0092075 | A1 | 5/2003 | Pepper | 435/7.9 |
| 2003/0113766 | A1 | 6/2003 | Pepper et al. | 435/6 |
| 2004/0091397 | A1 | 5/2004 | Picard | 422/99 |
| 2004/0132172 | A1 | 7/2004 | Cunningham et al. | 435/287.2 |
| 2004/0151626 | A1 | 8/2004 | Cunningham et al. | 422/58 |
| 2004/0223881 | A1 | 11/2004 | Cunningham et al. | 422/82.05 |
| 2004/0235198 | A1 | 11/2004 | Marx et al. | 436/527 |
| 2004/0263841 | A1 | 12/2004 | Caracci et al. | 356/300 |
| 2005/0070027 | A1 | 3/2005 | Gollier et al. | 436/518 |
| 2005/0100904 | A1 | 5/2005 | Yoshizato et al. | 435/6 |
| 2005/0158880 | A1 | 7/2005 | Ostuni et al. | 438/1 |
| 2005/0236554 | A1 | 10/2005 | Fontaine et al. | 250/208.1 |
| 2006/0063276 | A1 | 3/2006 | Jiang et al. | 436/518 |
| 2006/0205058 | A1 | 9/2006 | Frutos et al. | 435/287.1 |
| 2006/0205092 | A1 | 9/2006 | Lackritz et al. | 436/525 |
| 2006/0223051 | A1 | 10/2006 | Fang et al. | 435/4 |

FOREIGN PATENT DOCUMENTS

| WO | 2005005979 | * | 1/2005 |
|---|---|---|---|
| WO | WO 2005/005979 | | 1/2005 |
| WO | WO 2005/017507 | | 2/2005 |
| WO | WO2006/086883 | | 8/2006 |
| WO | WO2006/107506 | | 10/2006 |
| WO | WO 2006/107967 | | 10/2006 |
| WO | WO 2006/108183 | | 10/2006 |
| WO | WO 2007/015878 | | 2/2007 |
| WO | WO 2007/018872 | | 2/2007 |

OTHER PUBLICATIONS

Beske et al. (DDT 2002, vol. 7: S131-S135).*
Beske Oren et al, "A novel encoded particle technology that enables simultaneous interrogation of multiple cell types", Journal of Biomolecular Screening: The official Journal of the Society for Biomolecular Screening, vol. 9, No. 3, Apr. 2004, pp. 173-185.
Ye Fang et al, "Label-free cell-based assays for GPCR screening", Combinatorial Chemistry & High Throughput Screening, vol. 11, No. 5, Jun. 2008, pp. 357-369.
Hug, T. S., et al., "Optical waveguide lightmode spectroscopy as a new method to study adhesion of anchorage-dependent cells as an indicator of metabolic state", Biosensors & Bioelectronics 16 (2001), p. 865-874.
Li, S-Y., "Measurement of Adhesion and Spreading Kinetics of Baby Hamster Kidney and Hybridoma Cells Using an Integrated Optical Method", Biotechnol. Prog. 1994, 10, pg. 520-524.
Ramsden, J. J., "Optical Method for Measurement of Number and Shape of Attached Cells in Real Time", Cytometry 19, 1995, p. 97-102.
Hug, T. S., "Optical Waveguide Lightmode Spectroscopy (OWLS) to Monitor Cell Proliferation Quantitatively", Biotechnology and Bioengineering, vol. 80, No. 2, Oct. 20, 2002, p. 213-221.
Horvath, R., "Optical waveguide sensor for on-line monitoring of bacteria", Optics Letters, Jul. 15, 2003, vol. 28, No. 14, p. 1233-1235.
Hug, T. S., "Biophysical Methods for Monitoring Cell-Substrate Interactions in Drug Discovery", Assay and Drug Development Technologies, vol. 1, No. 3, 2003, p. 479-488.
Horvath, R., "Monitoring of living cell attachment and spreading using reverse symmetry waveguide sensing", Applied Physics Letters 86, (2005), 071101-1-071101-3.
Corso, C. D., "An investigation of antibody immobilization methods employing organosilanes on planar ZnO surfaces for biosensor applications", Biosensors and Bioelectronics 24, (2008), p. 805-811.

(Continued)

Primary Examiner — Kimberly Chong
(74) Attorney, Agent, or Firm — John L. Haack

(57) ABSTRACT

A method and apparatus, as defined herein, for use in compound screening, compound profiling, or both assays, for example, against two different cellular targets in, for example, a single cell-type.

13 Claims, 15 Drawing Sheets

OTHER PUBLICATIONS

M. Azzi et al., "β-Arrestin-mediated activation of MAPK by inverse agonists reveals distinct active conformations for G protein-coupled receptors", PNAS, Sep. 30, 2003, vol. 100, No. 20, pp. 11406-11411.

J.G. Baker et al., "Influence of Agonist Efficacy and Receptor Phosphorylation on Antagonsit Affinity Measurements: Differences between Second Messenger and Reporter Gene Responses", *Mol. Pharmacol.*, 2003, vol. 64, No. 3, pp. 679-688.

Brecht et al., "Optical Probes and Transducers*", *Biosensors and Bioelectronics*, vol. 10, 1995, pp. 923-936.

K. Choudhuri et al., "T-cell receptor triggering is critically dependent on the dimensions of its peptide-MHC ligand", *Nature*, vol. 436, Jul. 28, 2005, pp. 578-582.

Clerc et al., "Direct Inununosensing With an Integrated-Optical Output Grating Coupler", Sensors & Actuators B, vol. 40, 1997, pp. 53-58.

Drews, "Drug Discovery: A Historical Perspective", *Science*, Mar. 17, 2000, vol. 287, pp. 1960-1964.

G.L. Duveneck et al., "Novel Bioaffinity Sensors for Trace Analysis Based on Luminescence Excitation by Planar Waveguides", *Sensors and Actuators B*, vol. 38-39, 1997, pp. 88-95.

G.L. Duveneck et al., "Review on Fluorescence-Based Planar Waveguide Biosensors", *Proc. SPIE*, vol. 3858, 1999, pp. 59-71.

G.L. Duveneck et al., "Two-Photon Fluorescence Excitation of Macroscopic Areas on Planar Waveguides", *Biosensors and Bioelectronics*, vol. 18, 2003, pp. 503-510.

Ye Fang et al., "Cellular functions of cholesterol probed with optical biosensors", *Biochimica et Biophysica Acta*, vol. 1763, 2006, pp. 254-261.

Y. Fang et al., "Characteristics of Dynamic Mass Redistribution of Epidermal Growth Factor Receptor Signaling in Living Cells Measured with Label-Free Optical Biosensors", *Anal. Chem.*, vol. 77, 2005, pp. 5720-5725.

Y. Fang et al., "G-Protein-Coupled Receptor Microarrays", *ChemBioChem*, Oct. 4, 2002, vol. 3, No. 10, pp. 987-991.

Y. Fang, "Label-Free Cell-Based Assays with Optical Biosensors in Drug Discovery", *Assay and Drug Development Technologies*, vol. 4, No. 5, 2006, pp. 583-595.

Y. Fang et al., "Non-Invasive Optical Biosensor for Assaying Endogenous G Protein-Coupled Receptors in Adherent Cells", *Journal of Pharmacological and Toxicological Method*, vol. 55, 2007, pp. 314-322.

Y. Fang et al., "Optical biosensor differentiates signalling of endogenous $PAR_1$ and $PAR_2$ in A431 cells", *BMC Cell Biology*, 2007, vol. 8, No. 24, pp. 1-12, http://www.biomedcentral.com/1471-2121/8/24, 2007.

Ye Fang et al., "Optical Biosensor Provides Insights for Bradykinin B2 Receptor Signaling in A431 Cells", *FEBS Letters*, vol. 579, 2005, pp. 6365-6374.

Y. Fang et al., "Probing cytoskeleton modulation by optical biosensors", *FEBS Letters*, vol. 579, 2005, pp. 4175-4180.

Y. Fang et al., "Resonant Waveguide Grating Biosensor for Living Cell Sensing", *Biophysical Journal*, vol. 91, Sep. 2006, pp. 1925-1940.

I. Giaever et al., "Monitoring fibroblast behaviour in tissue culture with an applied electric field", *Proc. Natl. Acad Sci.*, Jun. 1984, vol. 81, pp. 3761-3764.

H.M. Grandin et al., "Waveguide Excitation Fluorescence Microscopy: A New Tool for Sensing and Imaging the Biointerface", *Biosensors and Bioelectronics*, vol. 21, 2006, pp. 1476-1482.

A. Grakoui et al., "The Immunological Synapse: A Molecular Machine Controlling T Cell Activation", *Science*, vol. 285, Jul. 9, 1999, pp. 221-227.

S.A. Green et al., "Sustained Activation of a G Protein-coupled Receptor via "Anchored" Agonist Binding", *The Journal of Biological Chemistry*, vol. 271, No. 39, pp. 24029-24035, 1996.

M. Halter et al., "Enhanced Optical Waveguide Light Mode Spectroscopy Via Detection of Fluorophore Absorbance", *Review of Scientific Instruments*, vol. 77, 2006, pp. 103105-1-6.

M. Hide et al., "Real-Time Analysis of Ligand-Induced Cell Surface and Intracellular Reactions of Living Mast Cells Using a Surface Plasmon Resonance-Based Biosensor", *Analytical Biochemistry*, vol. 302, 2002, pp. 28-37.

W.R. Holland et al., "Waveguide Mode Enhancement of Molecular fluorescence", *Optics Letters*, vol. 10, No. 8, Aug. 1985, pp. 414-416.

B. January et al., "$β_2$-Adrenergic Receptor Desensitization, Internationalization, and Phosphorylation in Response to Full and Partial Agonists", *The Journal of Biological Chemistry*, vol. 272, No. 38, pp. 23871-23879, 1997.

Jin et al., "A Biosensor Concept Based on Imaging Ellipsometry for Visualization of Biomolecular Interactions", *Analytical Biochemistry*, vol. 232, 1995, pp. 69-72.

C.E. Jordan et al., "Surface Plasmon Resonance Imaging Measurements of DNA Hybridization Adsorption and Streptavidin/DNA Multilayer Formation at Chemically Modified Gold Surfaces", *Anal. Chem.*, 1997, pp. 4939-4947.

Jordan et al., "Surface Plasmon Resonance Imaging Measurements of Electrostatic Biopolymer Adsorption Onto Chemically Modified Gold Surfaces", *Anal. Chem.*, 1997, vol. 69, pp. 1449-1456.

P. Lalanne et al., "Highly Improved Convergence of the Coupled-Wave Method for TM Polarization", *J. Opt Soc. Am. A*, vol. 13, No. 4, Apr. 1996, pp. 779-784.

G. Liapakis et al., "Synergistic Contributions of the Functional Groups of Epinephrine to its Affinity and Efficacy at the $β_2$ Adrenergic Receptor", *Mol. Pharmacol.*, 2004, vol. 65, No. 5, pp. 1181-1190, 2000.

G. Liapakis et al., "The Forgotten Serine", *The Journal of Biological Chemistry*, vol. 275, No. 48, pp. 37779-37788.

Z. Lu et al., "Epidermal Growth Factor-Induced Tumor Cell Invasion and Metastasis Initiated by Dephosphorylation and Downregulation of Focal Adhesion Kinase", *Molecular and Cellular Biology*, Jun. 2001, vol. 21, No. 12, pp. 4016-4031.

L. Lorenzelli, et al., "Bioelectrochemical signal monitoring of in-vitro cultured cells by means of an automated microsystem based on solid state sensor-array", *Biosensors and Bioelectronics*, 2003, vol. 18, pp. 621-626.

Ma et al., "From the Analyst's Couch: Value of Novelty?", *Nature Reviews, Drug Discovery*, vol. 1, Aug. 2002, pp. 571-572.

Morhard et al., "Immobilization of Antibodies in Micropatterns for Cell Detection by Optical Diffraction", *Sensors and Actuators B*, vol. 70, 2000, pp. 232-242.

K. Mossman et al., "Micropatterned supported membranes as tools for quantitative studies of the immunological synapse", *Chemical Society Reviews*, vol. 36, 2007, pp. 46-54.

P.M. Nellen et al., "Integrated Optical Input Grating Couplers as Biochemical Sensors", *Sensors and Actuators*, 1988, vol. 15, pp. 285-295.

Pierce et al., "Seven-Transmembrane Receptors", *Nature Reviews, Molecular Cell Biology*, vol. 3, Sep. 2002, pp. 639-650.

Ramsden et al., "Kinetics of Adhesion and Spreading of Animal Cells", *Biotechnology and Bioengineering*, vol. 43, 1994, pp. 939-945.

M.D. Salik et al., Resonant Excitation Analysis of Waveguide Grating Couplers, *Optics Communications*, vol. 193, Jun. 15, 2001, pp. 127-131.

M.A. Simmons, "Functional Selectivity, Ligand-Directed Trafficking, Conformation-Specific Agonism: What's in a Name?", *Molecular Interventions*, Jun. 2005, vol. 5, Issue 3, pp. 154-157.

"Signal Pathway Identification and Deconvolution", http://www.cellkey.com/apps2.html, Oct. 2, 2007.

E.A. Smith et al., "Surface Plasmon Resonance Imaging as a Tool to Monitor Biomolecular Interactions in an Array Based Format", *Applied Spectroscopy*, 2003, vol. 57, No. 11, pp. 320A-332A.

K. Solly et al., "Application of Real-Time Cell Electronic Sensing (RT-CES) Technology to Cell-Based Assays", *ASSAY and Drug Development Technologies*, 2004, vol. 2, No. 4, pp. 363-372.

G. Swaminath et al., "Probing the $β_2$ Adrenoceptor Binding Site with Catechol Reveals Differences in Binding and Activation by Agonists and Partial Agonists", *The Journal of Biological Chemistry*, vol. 280, No. 23, pp. 22165-22171, 2005.

Tiefenthaler et al., "Intregrated Optical Switches and Gas Sensors", *Optics Letters*, Apr. 1984, vol. 10, No. 4, pp. 137-139.

J.D. Urban et al., "Functional Selectivity and Classical Concepts of Quantitative Pharmacology", *The Journal of Pharmacology and Experimental Therapeutics*, vol. 320, No. 1, pp. 1-13, 2006.

E. Verdonk et al., "Cellular Dielectric Spectroscopy: A Label-Free Comprehensive Platform for Functional Evaluation of Endogenous Receptors", *ASSAY and Drug Development Technologies*, 2006, vol. 4, No. 5, pp. 609-619.

G. Voirin et al., "$Si_3N_4/SiO_2$/Si Waveguide Grating for Fluorescent Biosensors", *Proc. SPIE*, vol. 3620, 1999, pp. 109-116.

J. Vörös et al., "Optical Grating Coupler Biosensors", *Biomaterials*, vol. 23, 2002, pp. 3699-3710.

Z.H. Wang et al., "A Label-Free Multisensing Immunosensor Based on Imaging Ellipsometry", *Anal. Chem.*, 2003, vol. 75, pp. 6119-6123.

L.C. Waters et al., "Microchip Device for Cell Lysis, Multiplex PCR Amplification, and Electrophoretic Sizing", *Anal. Chem.*, 1998, vol. 70, pp. 158-162.

P.N. Zeller et al., "Single-Pad Scheme for Integrated Optical Fluorescence Sensing", *Biosensors & Bioelectronics*, vol. 15, 2000, pp. 591-595.

"Zeptosens—Bioanalytical Solutions", http://www.zeptosens.com/en/, Sep. 24, 2007.

\* cited by examiner

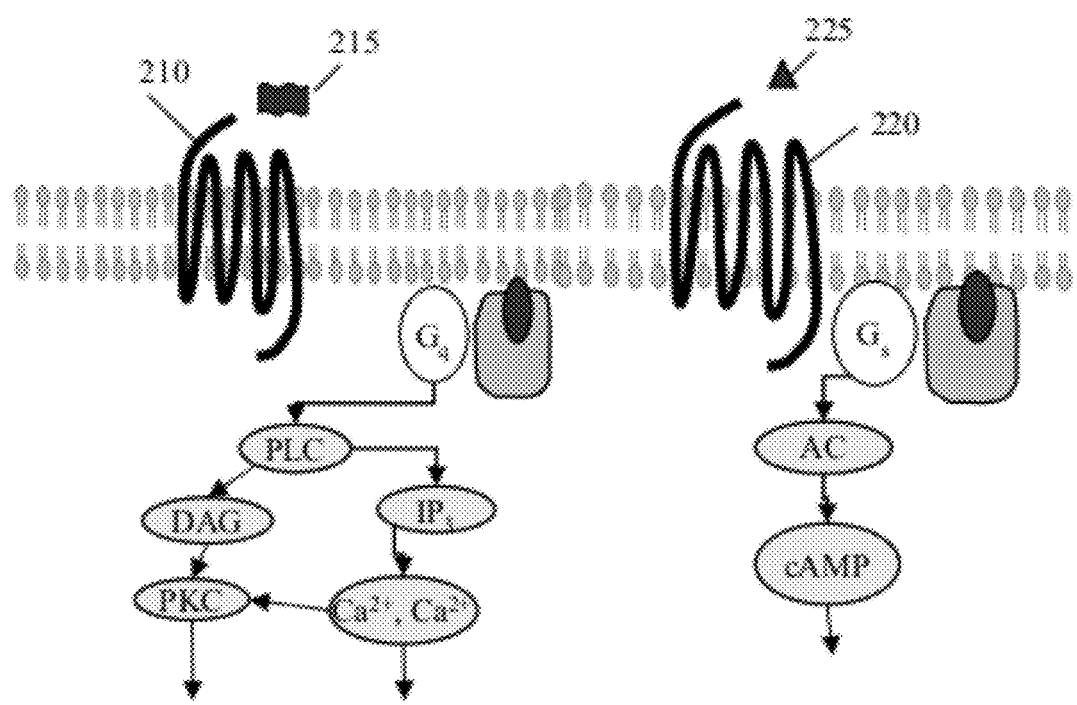

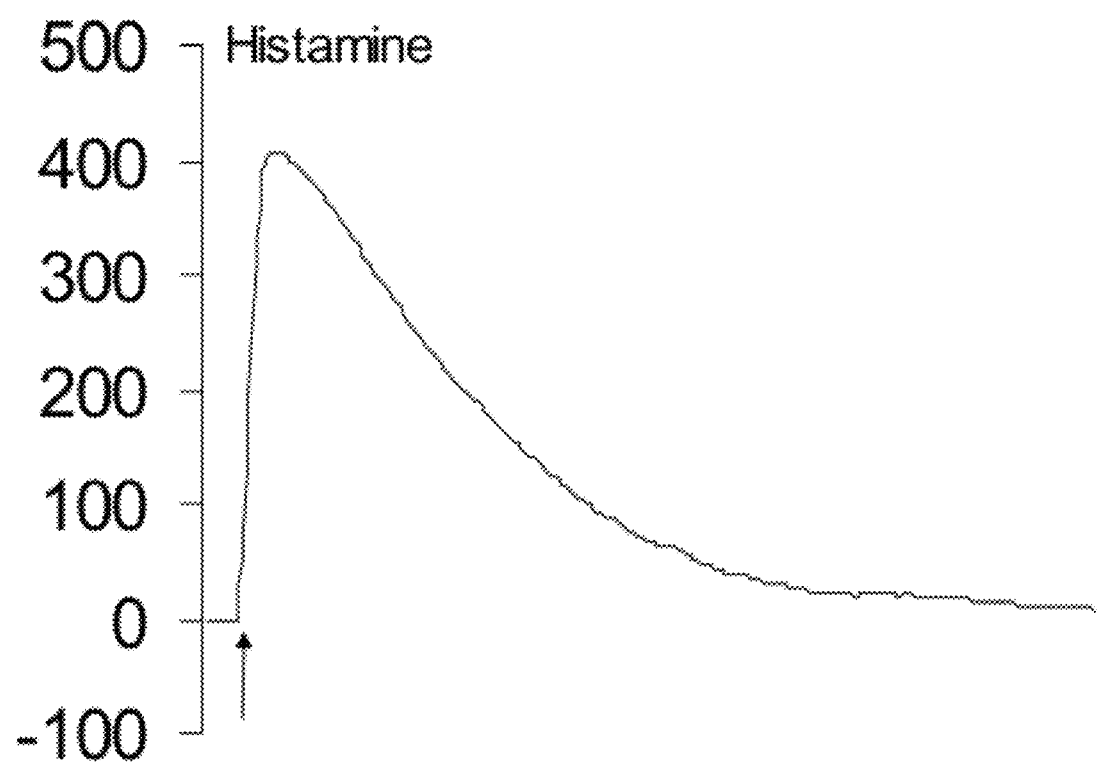

DUAL-TARGET BIOSENSOR CELL ASSAYS

CLAIMING BENEFIT OF PRIOR FILED U.S. APPLICATION

This application claims the benefit of U.S. Provisional Application Ser. No. 61/068,266, filed on Mar. 5, 2008. The content of this document and the entire disclosure of publications, patents, and patent documents mentioned herein are incorporated by reference.

BACKGROUND

The disclosure relates to biosensors, such as resonant waveguide grating (RWG) biosensors and electric impedance biosensors, for use in cell assay applications, for example, for compound screening and compound profiling.

SUMMARY

The disclosure provides a method and apparatus for use in cell assays for compound screening and compound profiling, for example, against two different cellular targets in a single cell-type, or against two different cellular targets, each of which is in a distinct cell-type.

BRIEF DESCRIPTION OF THE DRAWINGS

FIGS. 2A-2D show an exemplary RWG biosensor-based cell assays against two classes of G protein-coupled receptors (GPCRs), in embodiments of the disclosure.

FIGS. 7A-7F show results of an exemplary compound library screening for agonists using biosensor cellular assays, in embodiments of this disclosure.

DETAILED DESCRIPTION

Figure 1A:
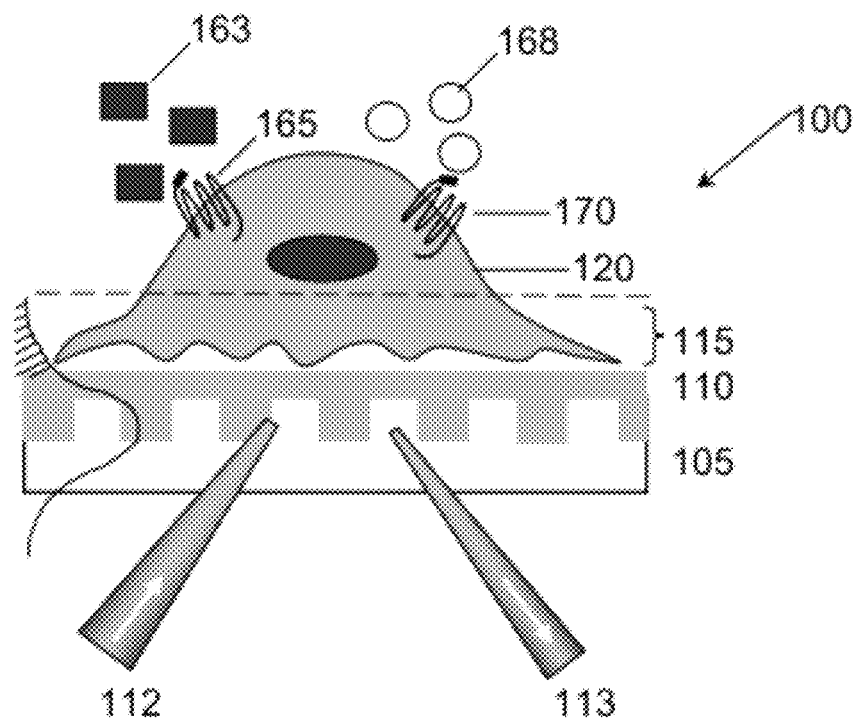
FIGS. 1A-1B show aspects of biosensor-based cell assays for dual- or duplexed-target specific screening using a RWG biosensor and electric biosensor, respectively, in embodiments of the disclosure.

Various embodiments of the disclosure will be described in detail with reference to drawings, if any. Reference to various embodiments does not limit the scope of the invention, which is limited only by the scope of the claims attached hereto. Additionally, examples in this specification are not limiting and merely set forth some of the many possible embodiments for the claimed invention.

Definitions

"Assay," "assaying" or like terms refers to an analysis to determine, for example, the presence, absence, quantity, extent, kinetics, dynamics, or type of a cell's optical or bio-impedance response upon stimulation with an exogenous stimuli, such as a ligand candidate compound.

"Attach," "attachment," "adhere," "adhered," "adherent," "immobilized", or like terms generally refer to immobilizing or fixing, for example, a surface modifier substance, a compatibilizer, a cell, a ligand candidate compound, and like entities of the disclosure, to a surface, such as by physical absorption, chemical bonding, and like processes, or combinations thereof. Particularly, "cell attachment," "cell adhesion," or like terms refer to the interacting or binding of cells to a surface, such as by culturing, or interacting with cells with a surface, such as a biosensor surface. The biosensor surface can be unmodified or modified, such as having a surface coating, an anchoring material, a compatibilizer (e.g., fibronectin, collagen, lamin, gelatin, polylysine, etc.), or like modifications that promote cell adhesion and cell status or growth. For suspension cells, the cells can be, for example, brought to contact with the detection zone of the biosensor through physical settlement during incubation, or through surface-cell interactions. The surface-cell interactions can be achieved by several means, e.g., covalently coupling of reactive surfaces with the basal cell membrane proteins or molecules, charge-based electrical interactions, binding of the sensor surface-presenting molecules (e.g., antibody, ligand) with the basal cell surface molecules, or like approaches.

"Adherent cells" refers to a cell or a cell line or a cell system, such as a prokaryotic or eukaryotic cell, that remains associated with, immobilized on, or in certain contact with the outer surface of a substrate. Such type of cells after culturing can withstand or survive washing and medium exchanging process, a process that is prerequisite to many cell-based assays. "Weakly adherent cells" refers to a cell or a cell line or a cell system, such as a prokaryotic or eukaryotic cell, which weakly interacts, or associates or contacts with the surface of a substrate during cell culture. However, these types of cells, for example, human embryonic kidney (HEK) cells, tend to dissociate easily from the surface of a substrate by physically disturbing approaches such as washing or medium exchange. "Suspension cells" refers to a cell or a cell line that is preferably cultured in a medium wherein the cells do not attach or adhere to the surface of a substrate during the culture. "Cell culture" or "cell culturing" refers to the process by which either prokaryotic or eukaryotic cells are grown under controlled conditions. "Cell culture" not only refers to the culturing of cells derived from multicellular eukaryotes, especially animal cells, but also the culturing of complex tissues, organs, or like systems.

"Cell" or like term refers to a small usually microscopic mass of protoplasm bounded externally by a semipermeable membrane, optionally including one or more nuclei and various other organelles, capable alone or interacting with other like masses of performing all the fundamental functions of life, and forming the smallest structural unit of living matter capable of functioning independently including synthetic cell constructs, cell model systems, and like artificial cellular systems.

"Cell system" or like term refers to a collection of cells and can include more than one type of cells (or differentiated forms of a single type of cell), which interact with each other, thus performing a biological or physiological or pathophysiological function. Such cell system can include, for example, an organ, a tissue, a stem cell, a differentiated hepatocyte cell, and like cell systems.

"Target" or like term refers to a cellular protein or biomolecule whose activation can mediate cell signaling or modulate cellular functions. A target can be, for example, a receptor, a phosphatase, a kinase, an enzyme, a DNA, an RNA, and like entities. A receptor can be, for example, a G protein-coupled receptor (GPCR), a receptor tyrosine kinase (RTK), a transporter, an ion channel, an integrin receptor, a sodium/proton exchanger, and like entities. A kinase can be, for example, protein kinase A, protein kinase C, mitogen-activated protein (MAP) kinases, an extracellular signal-regulated kinases, Src, Rho kinase, focal adhesion kinase, and like entities. An enzyme can be, for example, a membrane-bound adenylyl cyclase, a soluble adenylyl cyclase, a protease, and like entities.

"Dual-," "duplex," "duplexed-," or like terms refers to an assay that measures the cellular responses or activities mediated through two distinct targets, for example, a $G_q$-coupled receptor and a $G_s$-coupled receptor, two different $G_q$-coupled receptors, a GPCR and a receptor tyrosine kinase, a GPCR and an enzyme, a GPCR and a kinase, and like combinations.

"Multiplex," "multiplexed," or like terms refers to an assay that measures the cellular responses or activities mediated through more than two individual targets. The targets can belong to, for example, a same class of targets, for example, GPCRs, or different classes of targets, for example, two GPCRs and one receptor tyrosine kinase.

"Screen," "screening," or like terms refers to, for example, a systematic survey of one or more compounds or drug candidates or biologicals (e.g., RNAi, antibody) to examine their pharmacological activities acting on a particular target, a cell type, or a cell system. Pharmacological or biological activity is an expression describing the beneficial or adverse effects of a drug on living matter.

"Profile," "profiling," or like terms refers to an extrapolation of information about pharmacological activity of a drug candidate, a compound, or a biological acting on a living cell or cell system through one or more cellular targets, based on a known or predetermined signal output, such as the amplitude of an optical or bioimpedance response of cells, mediated through a particular target.

"Marker" or like term refers, for example, to a molecule, a biomolecule, or a biological that is able to modulate the activities of at least one cellular target (e.g., a $G_q$-coupled receptor, a $G_s$-coupled receptor, a $G_i$-coupled receptor, a $G_{12/13}$-coupled receptor, an ion channel, a receptor tyrosine kinase, a transporter, a sodium-proton exchanger, a nuclear receptor, a cellular kinase, a cellular protein, etc.), and result in a reliably detectable biosensor output as measured by a biosensor. Depending on the class of the intended cellular target and its subsequent cellular event(s), a marker could be an activator, such as an agonist, a partial agonist, an inverse agonist, for example, for a GPCR or a receptor tyrosine kinase or an ion channel or a nuclear receptor or a cellular enzyme adenylate cyclase. The marker could also be an inhibitor for certain classes of cellular targets, for example, an inhibitor or a disrupter for actin filament, or microtubule, or an inhibitor for a kinase such as Rho kinase, or an antibody, or like entities for a cell surface molecule, such as anti-epidermal growth factor receptor antibody.

"Detect" or like term refers to an ability of the apparatus and methods of the disclosure to discover or sense, simultaneously, at least two ligand-induced cellular responses, and to distinguish the sensed responses from an absence of the ligand compound.

"Identify" or like term refers to an ability of the apparatus and methods of the disclosure to not only recognize a ligand compound's impact on at least two targets but to also classify the nature of the ligand compound's impact or interaction on at least two targets.

"Stimulus," "therapeutic candidate compound," "therapeutic candidate," "prophylactic candidate," "prophylactic agent," "ligand candidate," or like terms refer to a molecule or material, naturally occurring or synthetic, which is of interest for its potential to interact with a cellular target immobilized or attached to the biosensor. A therapeutic or prophylactic candidate can include, for example, a chemical compound, a biological molecule, a peptide, a protein, a biological sample, a drug candidate small molecule, a drug candidate biologic molecule, a drug candidate small molecule-biologic conjugate, and like materials or molecular entity, or combinations thereof, which can specifically bind to or interact with at least one of two or more cellular targets such as a protein, DNA, RNA, an ion, a lipid, or like structure or component of a live-cell.

"Biosensor" or like term refers to an article, that in combination with appropriate apparatus, can detect a desired analyte. A biosensor can combine a biological component with a physicochemical detector component. A biosensor can typically consist of three parts: a biological component or element (such as tissue, microorganism, pathogen, cells, cell component, or combinations thereof), a detector element (operating in a physicochemical way such as optical, piezoelectric, electrochemical, thermometric, magnetic, or like manner), and a transducer associated with both components. In embodiments, the optical biosensor can convert a molecular recognition or molecular stimulation event in a live-cell into a quantifiable signal.

Abbreviations, which are well known to one of ordinary skill in the art, may be used (e.g., "h" or "hr" for hour or hours, "g" or "gm" for gram(s), "mL" for milliliters, and "rt" for room temperature, "nm" for nanometers, and like abbreviations).

"Include," "includes," or like terms means including but not limited to.

"About" modifying, for example, the quantity of an ingredient in a composition, concentrations, volumes, process temperature, process time, yields, flow rates, pressures, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods; and like considerations. The term "about" also encompasses amounts that differ due to aging of, for example, a composition, formulation, or cell culture with a particular initial concentration or mixture, and amounts that differ due to mixing or processing a composition or formulation with a particular initial concentration or mixture. Whether modified by the term "about" the claims appended hereto include equivalents to these quantities.

"Consisting essentially of" in embodiments refers, for example, to a composition, a method of making or using a composition, formulation, or composition on the surface of the biosensor, and articles, devices, or apparatus of the disclosure, and can include the components or steps listed in the claim, plus other components or steps that do not materially affect the basic and novel properties of the compositions, articles, apparatus, and methods of making and use of the disclosure, such as particular reactants, particular additives or ingredients, a particular agents, a particular cell or cell line, a particular surface modifier or condition, a particular ligand candidate, or like structure, material, or process variable selected. Items that may materially affect the basic properties of the components or steps of the disclosure or may impart undesirable characteristics to the present disclosure include, for example, decreased affinity of the cell for the biosensor surface, decreased affinity of the ligand candidate for a cell, decreased affinity of a pathogen for a cell, anomalous or contrary cell activity in response to a ligand candidate or like stimulus, and like characteristics. In some instances, the foregoing examples of undesirable characteristics can instead be highly desirable and beneficial in screening or profiling applications of the present disclosure, such as discovery of conditions or ligands that decrease the affinity of the ligand candidate for a cell, or decrease the affinity of a pathogen for a cell.

The indefinite article "a" or "an" and its corresponding definite article "the" as used herein means at least one, or one or more, unless specified otherwise.

Specific and preferred values disclosed for components, ingredients, additives, cell types, pathogens, and like aspects, and ranges thereof, are for illustration only; they do not exclude other defined values or other values within defined ranges. The compositions, apparatus, and methods of the disclosure include those having any value or any combination of the values, specific values, more specific values, and preferred values described herein.

The disclosure provides a method and apparatus for use in compound screening and compound profiling assays, for example, against two different cellular targets in a single cell-type.

In embodiments, the disclosure provides a multiplexed and target-specific screening method for compound profiling, screening, or both, using a label-free biosensor.

In embodiments, the screening method can comprise, for example:

providing a biosensor;
immobilizing a cell line sample expressing at least two different targets (e.g., a first target and a second target) onto the biosensor surface;
contacting, such as incubating, the cell line sample contacted with the biosensor with a ligand candidate for a time;
contacting, such as incubating, the ligand candidate-treated cell line with a mixture containing at least two markers, each marker can selectively modulate the activity of at least one of the different targets;
monitoring the biosensor output during the incubations; and
determining the effect of the ligand candidate on the mixture-induced biosensor output.

In embodiments, the target can be, for example, at least one of: a receptor, a cellular protein, or a combination thereof. The cellular protein can be, for example, at least one of a cellular enzyme, a cellular kinase, a cellular structural protein, or a combination thereof. The receptor can be, for example, at least one of a $G_q$-coupled receptor, a $G_s$-coupled receptor, a $G_i$-coupled receptor, a $G_{12/13}$-coupled receptor, a receptor tyrosine kinase, an ion channel, a sodium-proton exchanger, an integrin receptor, a transporter, or a combination thereof. In embodiments, the marker can be, for example, at least one of an agonist, a partial agonist, or an inverse agonist. In embodiments, the agonist can, for example, activate a target and produce a detectable biosensor output signal. In embodiments, the marker can be, for example, at least one of an inhibitor, or an antibody, where the marker can activate a target and produce a detectable biosensor output signal. In embodiments, each of the markers can specifically modulate the activity of a distinct target. In embodiments, the targets can be, for example, at least one of: a pair of $G_q$-coupled receptors, a pair of a $G_q$-coupled receptor and a $G_s$-coupled receptor, a pair of a $G_i$-coupled receptor and a $G_s$-coupled receptor, a pair of a G protein-coupled receptor and a receptor-tyrosine kinase, or a pair of a receptor and a cellular protein. In embodiments, the effect of the ligand candidate on the biosensor output can be, for example, to modulate of the marker-induced signal responses. In embodiments, the modulation can be, for example, a change in signal amplitude, dynamics, kinetics, or a combination thereof.

In embodiments, the screening method can comprise, for example:

providing a biosensor;
immobilizing a cell line sample expressing at least two different targets (i.e., a first target and a second target) onto the biosensor surface;
incubating the cell line sample with a cocktail solution containing at least one blocker that inhibits the activity of cellular proteins which are not the targets but interfere with the activity of the targets;
incubating the cell line sample contacted with the biosensor with a ligand candidate for a suitable time;
incubating the ligand candidate-treated cell line with a mixture containing at least two activators, each activator selectively activates one of the different targets;
monitoring the biosensor output during the incubations; and
determining the effect of the ligand candidate on the mixture-induced biosensor output.

In embodiments, the blocker(s) and the ligand candidate can be added separately or together. If added separately, the blocker(s) is(are) preferably added before the ligand candidate. The blocker can be, for example, an antagonist for a cellular protein, an inhibitor for a cellular protein, an interference RNA (RNAi) for a cellular protein, an anti-sense nucleic acid for a cellular protein, or like entities. In embodiments, the blocker, such as a solution, can be, for example, added before the ligand candidate. In embodiments, the blocker, such as a solution, can be, for example, added together with the ligand candidate.

In embodiments, the screening method can comprise, for example:

providing a biosensor;
immobilizing a mixed population of cells containing a first cell line expressing a first target and a second cell line expressing a second target onto the biosensor surface;
contacting, such as incubating, the immobilized mixed population of cells on the biosensor with a ligand candidate for a suitable or sufficient time;
incubating the ligand candidate-treated cell line with a mixture containing two activators, one activator selectively activates the first target, and the another activates the second target;
monitoring the biosensor output during the incubations; and
determining the effect of the ligand candidate on the mixture-induced biosensor output.

In embodiments, the two cell lines can be related each other, for example, a parental cell line and an engineered cell line using the parental cell. Alternatively, the two cells can be different in origin.

In embodiments, the screening method can comprise, for example:

providing a biosensor;
immobilizing a mixed population of cells containing a first cell line expressing a target and a second cell line not expressing the target onto the biosensor surface;

incubating the cell lines contacted with the biosensor with a ligand candidate for a suitable or sufficient time;

incubating the ligand candidate-treated cell lines with, for example, a solution containing an activator that selectively activates the target;

monitoring the biosensor output during the incubations; and determining the effect of the ligand candidate on the activator-induced biosensor output.

In embodiments, the two cell lines are preferably related each other, for example, an engineered cell expressing a GPCR, and a parental cell not expressing the GPCR. The seeding numbers of both cell lines can be predetermined such that after culture the desired ratio between the two types of cells can be, for example, about 1 to about 1. When the resultant mixed population of cells are stimulated with an activator for the target, the average response obtained will be about 50% compared to that using only the cells expressing the target. When a ligand candidate is also an activator specific to the target it can provide a comparable response as the activator. When a ligand candidate is an activator non-specific to the target it can provide a different response.

In embodiments, the screening method can comprise, for example:

providing a biosensor;

immobilizing a mixed population of cells containing a first cell line expressing a first target and a second cell line sample expressing a second target onto the biosensor surface;

incubating the cell line sample with a cocktail solution containing at least one blocker that inhibits the activity of cellular proteins that are not the targets but interfere with the activity of at least one of the targets;

incubating the cell line sample contacted with the biosensor with a ligand candidate for a suitable or sufficient time, for example to detect or measure any ligand interaction with the cell, or more specifically a cell target or receptor;

incubating the ligand candidate-treated cell line with a mixture containing at least two activators, each activator selectively activates one of the different targets; monitoring the biosensor output during the incubations; and determining the effect of the ligand candidate on the mixture-induced biosensor output.

In embodiments, the biosensor can be, for example, an optical biosensor, particularly a resonant waveguide grating biosensor or, for example, an electrical biosensor, particularly a bio-impedance biosensor. The cells can be a single cell-type, which expresses two distinct receptors, such as receptor A and receptor B (FIG. 1, 165, 170). Alternatively, the cells can be two different types of cells, each expressing one receptor, wherein the two types of cells can be mixed together before being placed on the sensor surface. Both receptors can belong to the same type of receptors (e.g., $G_q$-coupled receptors), different types of receptors, such as a pair of $G_q$ and $G_s$-coupled receptors, a pair of GPCR and receptor tyrosine kinase, or like receptor combinations. When the two receptors lead to similar signaling pathways, the concentrations of their corresponding activators can be preferably around their $EC_{50}$ values (i.e., a concentration of activator that binds to and activates the receptor, leading to 50% of its maximal response). When the two receptors lead to different signaling pathways, the concentrations of their corresponding activators can be over a wide range, e.g., from about $EC_{10}$ to about $10 \times EC_{100}$, or higher.

In embodiments, the disclosure provides a method that uses a combination of two different agonists or activators, each activating a different target, for compound screening and profiling. The method can be useful for target-specific based screening and profiling, and is particularly well suited for duplexed or multiplexed receptor or target screening.

In embodiments the present disclosure provides multiplexed target-specific compound screening and profiling in a live-cell environment using a label-free biosensor, such as a RWG biosensor or an electric impedance biosensor. The disclosure eliminates the need for cell engineering, or like manipulations, and eliminates the need for having the same target classes that require similar or identical cell signaling pathways, such as $Ca^{2+}$ mobilization. However, engineered cells or manipulation of cells can be used.

In embodiments, the targets can belong to the same family (e.g., $G_q$-coupled receptors), or distinct families (e.g., one can be a $G_q$-coupled receptor, another is a $G_s$-coupled receptor; alternatively, one can be a $G_s$-coupled receptor, another can be a $G_i$-coupled receptor; a pair of a G protein-coupled receptor and a receptor tyrosine kinase; a pair comprising a receptor and an intracellular kinase such as protein kinase C; or a pair of an intracellular kinase such as a protein kinase C and an enzyme such as adenylyl cyclase).

In embodiments, the activators or markers can be agonists for receptors, or activators for kinases or enzymes. For a given cell or cell system, a panel of activators, each of which can result in a reliable and detectable biosensor signal, can be predetermined and selected. For example, when an optical biosensor such as RWG biosensor is used, in human epidermoid carcinoma A431 cells a panel of activators can be selected from the following group or groups:

An agonist or a partial agonist for endogenous GPCRs can be, for example, bradykinin for bradykinin B2 receptor, epinephrine for β2 adrenergic receptor, adenosine for adenosine A2B receptor, thrombin or SFLLR-amide for protease activated receptor subtype 1, trypsin or SLIGKV-amide for protease activated receptor subtype 2, histamine for histamine H1 receptor, adenosine triphosphate (ATP) for P2Y receptors, lysophosphatidic acid (LPA) for LPA receptors, see for example, Fang, Y., et al., *J. Pharmacol. Tox. Methods,* 2007, 55, 314-322.

An agonist for endogenous receptor tyrosine kinase can be, for example, epidermal growth factor (EGF) for EGFR, see for example, Fang, Y., et al., *Anal. Chem.,* 2005, 77, 5720-5725.

An ion channel opener for an endogenous ion channel can be, for example, pinacidil for ATP-sensitive potassium ion channel.

An activator for a cellular enzyme can be, for example, forskolin for adenylate cyclase.

An activator for a cellular kinase can be, for example, 12-deoxyphorbol 13-acetate and phorbol 12-myristate 13-acetate for protein kinase C; or 8-bromo-cAMP and Sp-cAMPS and dibutyryl-cAMP for protein kinase A.

A disrupting agent can be, for example, cytochalasin D for actin filament, or nocodozale for microtubules.

An activator for integrin receptor can be, for example, soluble fibronectin or its fragments.

A cell membrane disrupting agent can be, for example, saponin to cause cell membrane leakage, see for example, Fang, Y., et al., *FEBS Lett.,* 2005, 579, 4175-4180.

An apoptotic inducer can be, for example, $Ca^{2+}$ ionophore A23187 to trigger a $Ca^{2+}$ dependent cell apoptosis.

A kinase inhibitor can be, for example, Y-27632 for Rho kinase.

Since stimulation of the cells examined with each marker leads to a specific cellular event, a signaling pathway, or signaling network interactions, and each signaling pathway may involve distinct sets of cellular targets, the selected panel of markers will cover many, if not all, of the cellular signaling pathways in the given cell system.

In embodiments the disclosure provides methods for target-specific multiplexed screening and profiling of compounds using biosensors. Significant attributes of the disclosed method includes, for example:

an applicability to either optical biosensors or electric impedance biosensors in cell-based assays;

at least a doubling of the assay throughput;

broad applicability to different classes of targets which can be assayed simultaneously in a single assay; and the method can be suitable for measuring receptor-receptor interactions.

The receptor-receptor interactions can occur different levels, for example, dimerization of the two receptors, oligomerization of the receptors, cross-talk through their down-stream signaling cascades, or like interactions, and combinations thereof. Conventional cell-based assays rely on the measurement of a specific cellular event mediated through a target receptor, such as a G protein-coupled receptor. Because of that dimension, together with the knowledge that different classes of target receptors result in distinct cell signaling in a given cell-type, screening against multiple target receptors largely remains elusive.

Although standard screening campaigns, which typically can involve assaying a single target at a time, have been successful for identifying potent drug candidates, very little information about compound selectivity is generated. Currently, selectivity studies are conducted downstream in the drug discovery process. However, discarding compounds at later stages because of adverse binding makes the drug discovery process more expensive and time consuming. Multi-target screens that examine the activity of compounds against multiple targets in parallel could be extremely beneficial in efficiently addressing compound selectivity at an early stage in the drug discovery process.

Common multiplexed screening methods are typically based on microarray technology, which has become a versatile tool for the simultaneous analysis of many genes and proteins in a single experiment. The use of protein microarrays has been extended from profiling protein abundance to determining, for example, the location, modification, and interaction of proteins with other chemical and biological molecules. These developments have created a new paradigm in the drug discovery and development processes. Examples of microarrays for compound profiling and screening include, for example, air-stable GPCR microarrays, see for example, Fang, Y., et al., "Membrane protein microarrays", *Journal of the American Chemical Society*, 2002, 124, 2394-2395; Fang, Y., et al., "Air-stable G protein-coupled receptor microarrays and ligand binding characteristics", *Analytical Chemistry*, 2006, 78, 149-155, cell arrays using cells cultured on bar-coded CellCard carriers, see for example, Beske, O., et al., "A novel encoded particle technology that enables simultaneous interrogation of multiple cell types," *Journal of Biomolecular Screening*, 2004, 9, 173-185, or transfected cell cluster arrays using solid state transfection, see for example, Mishina, Y. M., et al., "Multiplex GPCR assay in reverse transfection cell microarrays," *Journal of Biomolecular Screening*, 2004, 9,196-207. These technologies generally require the engineering or manipulation of cells, such as purified cell membrane fragments from lysed cells having a target receptor over-expressed for GPCR microarrays, or transfections for cell cluster arrays, or distinct types of cells or engineered variants of a single type of cells for CellCard technology.

Duplexed functional assays have also been developed based on $Ca^{2+}$ flux measurements, for example, by mixing two stably transfected cell populations in the right proportions, where each population expresses a target. If there is a "hit" that can activate one receptor, it can result in 50% of the fluorescence signal using, for example, a FLIPR (fluorometric imaging plate reader) system. Additionally, a "hit" could result in 100% of the signal if another hit has cross-activity and can activate the two receptors. Such a screen would double the potential hits generated using a single-target screen. However, additional screens would be needed using a single-target screen to de-convolute the hits. Such a duplexed assay is only limited to two $G_q$-coupled receptors in which both mediate signaling through $G_q$ and subsequent $Ca^{2+}$ mobilization.

In embodiments the disclosure provides a label-free screening method comprising:

providing an biosensor having a mixed population of cells containing two types of cells co-immobilized on a surface of the biosensor;

contacting the immobilized cells with a ligand candidate; and determining the ligand candidate-induced biosensor output.

The two types of cells can be, for example, a parental cell and an engineered cell expressing a target; two engineered cells each expressing a target; or two native cells.

In embodiments the disclosure provides a label-free screening method comprising:

providing a biosensor having a mixed population of cells containing a first type of cells expressing a first target and a second type of cells expressing a second target, both cell types are co-immobilized on a surface of the biosensor;

contacting the immobilized cells with a ligand candidate;

contacting the ligand candidate-treated cells with a mixture containing two markers, each marker specifically modulating the activity of a target; and determining the effect of the ligand candidate on the marker mixture-induced biosensor output.

1. Label-free Biosensor-based Cell Assays

Label-free cell-based assays generally employ a biosensor to monitor ligand-induced responses in living cells. A biosensor typically utilizes a transducer such as an optical, electrical, calorimetric, acoustic, magnetic, or like transducer, to convert a molecular recognition event or a ligand-induced change in cells contacted with the biosensor into a quantifiable signal. These label-free biosensors can be used for molecular interaction analysis, which involves characterizing how molecular complexes form and disassociate over time, or for cellular response, which involves characterizing how cells respond to stimulation. FIG. 1 highlights two types of biosensors that are currently used as the basis for label-free cell-based assays, resonant waveguide grating (RWG) biosensors and electrical biosensors, and how to use biosensor-based cell assays for dual target-based screening and profiling of compounds.

RWG biosensors and systems—An RWG biosensor can include, for example, a substrate (e.g., glass), a waveguide thin film with an embedded grating structure, and a cell layer (FIG. 1a). The RWG biosensor utilizes the resonant coupling of light into a waveguide by means of a diffraction grating, leading to total internal reflection at the solution-surface interface, which in turn creates an electromagnetic field at the interface. This electromagnetic field is evanescent in nature, meaning that it decays exponentially from the sensor surface; the distance at which it decays to 1/e of its initial value is known as the penetration depth and is a function of the design of a particular RWG biosensor, but is typically on the order of about 200 nm. This type of biosensor exploits such evanescent waves to characterize ligand-induced alterations of a cell layer at or near the sensor surface.

RWG instruments can be subdivided into systems based on angle-shift or wavelength-shift measurements. In a wavelength-shift measurement, polarized light covering a range of incident wavelengths with a constant angle is used to illuminate the waveguide; light at specific wavelengths is coupled into and propagates along the waveguide. Alternatively, in angle-shift instruments, the sensor is illuminated with monochromatic light and the angle at which the light is resonantly coupled is measured. The resonance conditions are influenced by the cell layer (e.g., cell confluency, adhesion and status), which is in direct contact with the surface of the biosensor. When a ligand or an analyte interacts with a cellular target (e.g., a GPCR, a kinase) in living cells, any change in local refractive index within the cell layer can be detected as a shift in resonant angle (or wavelength).

The Corning® Epic® system uses RWG biosensors for label-free biochemical or cell-based assays (Corning Inc., Corning, N.Y.). The Epic® System consists of an RWG plate reader and SBS (Society for Biomolecular Screening) standard microtiter plates. The detector system in the plate reader exploits integrated fiber optics to measure the shift in wavelength of the incident light, as a result of ligand-induced changes in the cells. A series of illumination-detection heads are arranged in a linear fashion, so that reflection spectra are collected simultaneously from each well within a column of a 384-well microplate. The whole plate is scanned so that each sensor can be addressed multiple times, and each column is addressed in sequence. The wavelengths of the incident light are collected and used for analysis. A temperature-controlling unit can be included in the instrument to minimize spurious shifts in the incident wavelength due to the temperature fluctuations.

Figure 1B:
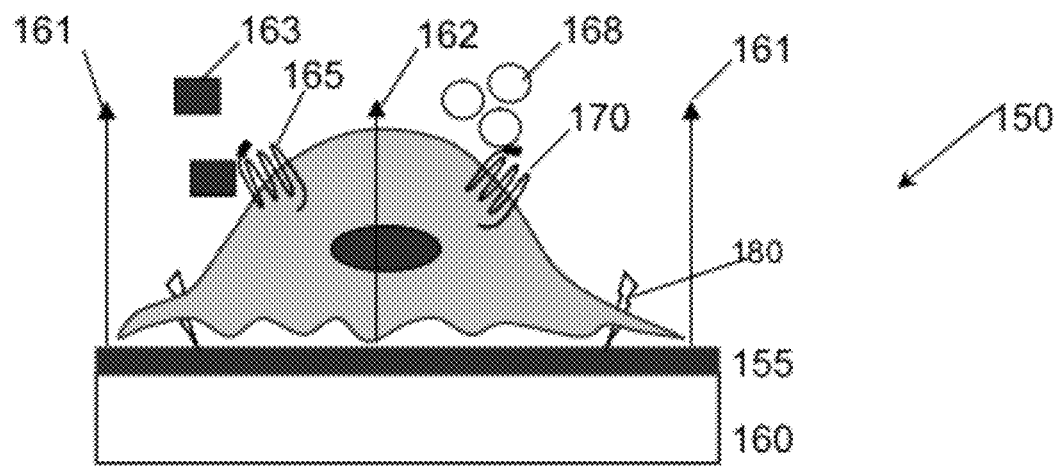

Electrical biosensors and systems—Electrical biosensors consist of a substrate (e.g., plastic), an electrode, and a cell layer (FIG. 1b). In this electrical detection method, cells are cultured on small gold electrodes arrayed onto a substrate, and the system's electrical impedance is followed with time. The impedance is a measure of changes in the electrical conductivity of the cell layer. Typically, a small constant voltage at a fixed frequency or varied frequencies is applied to the electrode or electrode array, and the electrical current through the circuit is monitored over time. The ligand-induced change in electrical current provides a measure of cell response. Impedance measurement for whole cell sensing was first realized in 1984. Since then, impedance-based measurements have been applied to study a wide range of cellular events, including cell adhesion and spreading, cell micromotion, cell morphological changes, and cell death. Classical impedance systems suffer from high assay variability due to use of a small detection electrode and a large reference electrode. To overcome this variability, the latest generation of systems, such as the CellKey system (MDS Sciex, South San Francisco, Calif.) and RT-CES (ACEA Biosciences Inc., San Diego, Calif.), utilize an integrated circuit having a microelectrode array.

The CellKey system consists of an environmentally controlled impedance measurement system, a 96-well electrode-embedded microtiter plate, an onboard 96-well fluidics, and custom acquisition and analysis software. The cells are seeded in the culture wells; each well has an integrated electrode array. The system operates using a small-amplitude alternating voltage at 24 frequencies, from 1 KHz to 10 MHz. The resultant current is measured at an update rate of 2 sec. The system is thermally regulated and experiments can be conducted, e.g., between 28° C. and 37° C. A 96-well head fluid delivery device handles fluid additions and exchanges onboard.

The RT-CES system can include four main components: electronic microtiter plates (E-Plate™), E-Plate station, electronic analyzer, and a monitoring system for data acquisition and display. The electronic analyser sends and receives the electronic signals. The E-Plate station is placed inside a tissue culture incubator. The E-Plate station comes in three throughput varieties: a 16× station for running six 16-well E-Plates at a time, a single 96-well E-Plate station, and the Mult-E-Plate™ station, which can accommodate up to six 96-well E-Plates at a time. The cells are seeded in E-Plates, which are integrated with microelectronic sensor arrays. The system operates at a low-voltage (less than 20 mV) AC signal at multiple frequencies.

Optical signals of GPCR activation with RWG biosensor— Cells are dynamic objects with relatively large dimensions, e.g., typically tens of microns. RWG biosensors enable detection of ligand-induced changes within the bottom portion of cells, determined by the penetration depth of the evanescent wave. Furthermore, the spatial resolution of an optical biosensor is determined by the spot size (about 100 microns) of the incident light source. Thus, a highly confluent cell layer is generally used in order to achieve optimal assay results; and the sensor configuration can be viewed as a three-layer waveguide composite, including, for example, a substrate, waveguide thin film, and a cell layer. Following a 3-layer waveguide biosensor theory in combination with cellular biophysics, we found that for whole-cell sensing, a ligand-induced change in effective refractive index, the detected signal $\Delta N$, is governed by equation (1):

$$\Delta N = S(N)\Delta n_C \quad (1)$$
$$= S(N)\alpha d \sum_i \Delta C_i \left[ e^{\frac{-z_i}{\Delta Z_C}} - e^{\frac{-z_{i+1}}{\Delta Z_C}} \right]$$

where $S(C)$ is the system sensitivity to the cell layer, and $\Delta n_c$ is the ligand-induced change in local refractive index of the cell layer sensed by the biosensor. $\Delta Z_c$ is the penetration depth into the cell layer, $\alpha$ is the specific refractive index increment (about 0.18/mL/g for proteins), $z_i$ is the distance where the mass redistribution occurs, and d is an imaginary thickness of a slice within the cell layer. Here the cell layer is divided into an equally-spaced slice in the vertical direction. We assumed that the detected signal is, to a first order, directly proportional to the change in refractive index of the bottom portion of cell layer $\Delta n_c$. The $\Delta n_c$ in turn is directly proportional to changes in local concentration of cellular targets or molecular assemblies within the sensing volume, given the refractive index of a given volume within cells is largely determined by the concentration of biomolecules, mainly proteins. A weighted factor $\exp(-z_i/\Delta Z_c)$ is taken into account for a change in local protein concentration that occurs, considering the exponentially decaying nature of the evanescent wave. Thus, the detected signal is the sum of mass redistribution occurring at distinct distances away from the sensor surface, each with unequal contribution to the overall response. Eq. (1) suggests that the detected signal with an RWG biosensor is sensitive primarily to the vertical mass redistribution, as a result of a change in local protein concentration. The detected signal is often referred to as a dynamic mass redistribution (DMR) signal.

GPCR activation leads to a series of spatial and temporal events, including, for example, ligand binding, receptor activation, protein recruitment, receptor internalization and recycling, second messenger alternation, cytoskeletal remodeling, gene expression, and cell adhesion changes. Each cellular event has its own characteristics regarding its kinetics, duration, amplitude, and mass movement. Thus it is reasonable to assume that these cellular events may contribute differently to the overall DMR signal, depending on where they occur. Using a panel of agonists targeting a variety of GPCRs, we have identified three classes of DMR signals in human epidermoid carcinoma A431 cells, which reflect the signaling pathways mediated. Since each is correlated with the activation of a class of GPCRs depending on the G protein with which the receptor is coupled, the DMR signals obtained were named $G_q$-, $G_s$- and $G_i$-DMR signals, respectively. Each class of DMR signals exhibits distinct kinetic and dynamic characteristics, reflecting the unique signaling integration mediated through different classes of GPCRs. The unique characteristics of the DMR signals can be used to identify the G-protein coupling mechanism of orphan GPCRs.

Bioimpedance signals of GPCR activation—In a typical impedance-based cell assay, cells are brought into contact with a gold electrode arrayed on the bottom of culture wells. The total impedance of the sensor system is determined primarily by the ion environment surrounding the biosensor. Under application of an electrical field, the ions undergo field-directed movement and concentration gradient-driven diffusion. For whole cell sensing, the total electrical impedance has four components: the resistance of the electrolyte solution; the impedance of the cell; the impedance at the electrode/solution interface; and the impedance at the electrode/cell interface. In addition, the impedance of a cell comprises two components: the resistance; and the reactance. The conductive characteristics of cellular ionic strength provide the resistive component, whereas the cell membranes, acting as imperfect capacitors, contribute a frequency-dependent reactive component. Thus, the total impedance is a function of many factors, including, for example, cell viability, cell confluency, cell numbers, cell morphology, degree of cell adhesion, ionic environment, the water content within the cells, the detection frequency, and like considerations.

In the RT-CES system, a percentage of this small voltage applied is coupled into the cell interior. Such signals applied to cells are believed to be much smaller than the resting membrane potential of a typical mammalian cell and thus present minimal or no disturbance to cell function. The RT-CES system measures these changes in impedance and displays it as a parameter called the cell index. The cell index is calculated according to the equation (2):

$$CI = \max_{i=1,\ldots,N}\left(\frac{R_{cell}(f_i)}{R_0(f_i)} - 1\right) \quad (2)$$

where N is the number of frequency points at which the impedance is measured (e.g., N=3 for 10 kHz, 25 kHz, and 50 kHz), and $R_0(f)$ and $R_{cell}(f)$ are the frequency electrode resistance without cells or with cells present in the wells, respectively.

In the CellKey system, a change in sensor system's impedance is attributed to a change in complex impedance (delta Z or dZ) of a cell layer that occurs in response to receptor stimulation. At low frequencies, the small voltage applied induces extracellular currents (iec) that pass around individual cells in the layer. However, the conduction currents through cell membrane due to ion channels may also be important at low measurement frequencies. At high frequencies, they induce transcellular currents (itc) that penetrate the cellular membrane (FIG. 1b). The ratio of the applied voltage to the measured current for each well is its impedance (Z) as described by Ohm's law.

When cells are exposed to a stimulus, such as a receptor ligand, signal transduction events are activated that lead to complex cellular events such as modulation of the actin cytoskeleton that cause changes in cell adherence, cell shape and volume, and cell-to-cell interaction. These cellular changes individually or collectively affect the flow of extracellular and transcellular current, and therefore, affect the magnitude and characteristics of the measured impedance. For example, a CellKey system was used to identify the impedance responses of cells mediated through the activation of distinct classes of GPCRs. Results showed that there are three types of impedance signals mediated through the activation of three classes of GPCRs, depending on the G protein to which the receptor is coupled. Similar profiles were also recorded using the RT-CES system. Although not limited by theory it is believed that these impedance signals are due to the different effects on the actin cytoskeleton that affect the cellular parameters measured by impedance, in response to the activation of different classes of GPCRs. It has been shown that activation of $G_q$ and $G_i$ GPCRs leads to increased actin polymerization, while stimulation of $G_s$ GPCRs leads to actin depolymerization.

Both optical and electrical biosensors are applicable to many distinct classes of targets, including GPCRs, receptor tyrosine kinases, kinases, enzymes, or other cellular targets.

2. Duplexed Target-specific Screening Using Biosensor-based Cell Assays

The biosensor-based cell assays are capable of multiplexing. The activation of a same class of targets (e.g., $G_q$-coupled receptors) in a given cell line leads to almost identical optical signatures, suggesting that multiple targets within the same family can be assayed at the same time. For example, A431 cells endogenously express bradykinin $B_2$ receptor, P2Y receptors, and protease activated receptors (PARs). Upon stimulation with bradykinin, ATP, or thrombin, quiescent A431 cells respond with similar $G_q$-type optical signatures. The quiescent state is obtained through continuous culturing using a serum-free medium for about 20 hours. Fluo-3 assays show that the activation of all three receptors mediates $G_q$-signaling. These observations suggest that biosensor-based assays can be used to screen compounds or hits that can activate same classes of receptors, which are expressed within the same cells.

G protein-coupled receptors (GPCRs) are the richest class of drug targets in the human genome and remain a popular target for the pharmaceutical industry. About 30 known GPCRs are the targets for about 40% of all currently marketed drugs and many other functionally uncharacterized GPCRs are potentially druggable targets and represent an untapped resource in drug discovery. Efforts to bring new GPCR drugs to the market has prompted a revolution in assay methods, particularly functional cellular assays. However, current assays are mostly pathway-biased and only measure "points of contact" in GPCR signaling cascades. Given the recent realization of the complexity of GPCR signaling and of the ligand-directed functional selectivity, these pathway-biased assays tend to result in false negatives. Furthermore, many conventional assays typically assay a single target at a time because of their limited capacity for multiplexing and their pathway-biased nature. Multi-target screens that can examine the activity of compounds against multiple targets simultaneously are logically suited to address compound selectivity.

Label-free optical biosensors including surface plasmon resonance (SPR), resonant waveguide grating (RWG), and plasmon-waveguide resonance (PWR) are routinely used for biomolecular interaction analysis. Recently, label-free optical biosensors were applied for whole cell sensing, and these biosensors are capable of monitoring endogenous receptor activation, leading to high-information and physiologically relevant measures of a receptor-ligand pair (see Fang, Y. et al. "Resonant waveguide grating biosensor for living cell sensing", *Biophys. J.*, 2006, 91, 1925-1940). These assays do not require prior knowledge of cell signaling, and are pathway-unbiased (see Fang, Y. et al., "Non-invasive optical biosensor for assaying endogenous G protein-coupled receptors in adherent cells", *J. Pharmacol Toxicol. Methods*, 2007, 55, 314-322). The optical responses recorded are pathway-sensitive, and reflect the complexity of receptor signaling (see Fang, Y., et al., "Optical biosensor provides insights for bradykinin B2 receptor signaling in A431 cells", *FEBS Lett.*, 2005, 579, 6365-6374).

Referring to the figures, FIG. 1 show principles of biosensor-based cell assays and duplexed target-specific screening. FIG. 1a shows an RWG biosensor for monitoring ligand-induced dynamic mass redistribution (DMR) in living cells (100). Cells can be directly cultured onto the surface of the biosensor, or brought to contact with the sensor surface. In embodiments, the biosensor can include, for example, a glass substrate (105), a waveguide (110) thin film within which a grating structure is embedded, a light source (112), and means to detect and process the resulting refracted light (113). Only the mass redistribution within the detection zone (115) and the bottom portion of cells (120) is directly measured. FIG. 1b is an electric biosensor for monitoring the ionic environment surrounding the biosensor and the cells (150). Cells can be cultured on the surface of a biosensor having, for example, arrayed gold microelectrode(s) (155) on a substrate (160). Both extracellular (161) and transcellular (162) current flows can be measured, while a low AC voltage at variable frequencies (e.g., electric pulse (180)) is applied to the cell. In FIGS. 1a and 1b the squares (■) represent a ligand (163) for Receptor A (165), while circles (○) represent a ligand (168) for Receptor B (170). Both receptors A and B are expressed in the same cell.

Experimental Procedures

Materials

The LOPAC was purchased from Sigma Chemical Co. (St. Louis, Mo.). S(−)epinephrine, dopamine, norepinephrine, and histamine were obtained from Tocris (St. Louis, Mo.). (±)-brompheniramine maleate, (±)chlorpheniramine maleate, clemizole hydrochloride, clemastine fumarate, diphenhydramine hydrochloride, or triprolidine hydrochloride, SKF91488 dimaleate, ranitidine hydrochloride, catechol and thioperamide maleate were purchased from Sigma (St. Louis, Mo.). SFFLR-amide was obtained through Bachem (King of Prussia, Pa.). Cell culture compatible Epic® 384-well RWG (resonant waveguide grating) biosensor microplates were obtained from Corning Inc (Corning, N.Y.).

Cell Culture

Human epidermoid carcinoma A431 cells (American Type Cell Culture) were grown in Dulbecco's modified Eagle's medium (DMEM) supplemented with 10% fetal bovine serum (FBS), 4.5 g/liter glucose, 2 mM glutamine, and antibiotics. About $1.8 \times 10^4$ cells at passage 3 to 15 suspended in 50 μL the medium containing 10% FBS were placed in each well of a 384-well microplate, and were cultured at 37° C. under air/5% $CO_2$ for about 1 day, followed by about 20 hr starvation through continuously culture in the serum-free DMEM.

Optical Biosensor System and Cell Assays

Corning® Epic® wavelength interrogation system was used. This system consists of a temperature-control unit, an optical detection unit, and an on-board liquid handling unit with robotics. The detection unit is centered on integrated fiber optics, and enables kinetic measures of cellular responses with a time interval of about 7 or about 15 sec.

The RWG biosensor exploits its evanescent wave, created by the total internal reflection of light at a solution-surface interface, to measure ligand-induced dynamic mass redistribution (DMR) signals in cells. The evanescent wave extends into the cells and exponentially decays over distance, leading to a characteristic sensing volume of about 150 nm, implying that any optical response mediated through the receptor activation only represents an average over the portion of the cell that the evanescent wave is sampling. Such sampling with the biosensor is sufficient to differentiate the signaling of distinct classes of GPCRs in living cells, and offers a simplified representation of GPCR signaling.

Like SPR, the RWG biosensor is sensitive to refractive index—an intrinsic property of biomolecules. Since the refractive index of a given volume within a cell is largely determined by the concentrations of bio-molecules such as proteins, we found, based on a three-layer waveguide grating theory, that a ligand-induced optical response is largely associated with dynamic mass redistribution. The relocation of cellular targets towards the sensor surface (e.g., relocation of intracellular targets to the activated receptors at the basal membrane surface) makes a positive contribution to the DMR (P-DMR); conversely, the movement of cellular targets away from the sensor surface (e.g., receptor internalization) is a negative contributor to the DMR (N-DMR). The aggregation of these events determines the kinetics and amplitudes of a ligand-induced DMR. However, recent studies, using PWR technology and in vitro reconstituted GPCRs immobilized onto the sensor surface, showed that a ligand-induced optical response of the receptor-lipid membrane system consists of two components—changes in mass density and changes in structure. Since the RWG biosensor used here is unable to differentiate the contributions of these components, ligand-induced changes in organization of biomolecules in living cells may also contribute to the overall response measured.

For biosensor cellular assays, a 2 min baseline was first established. Compound solutions were then transferred into the sensor plate having cells maintained in Hanks balanced salt solution (20 mM Hepes, pH 7.1), and the cell responses were recorded continuously for one hour. Afterwards, a second baseline (about 2 min) was established, the cocktail solution containing 2 nM epinephrine and 500 nM histamine was introduced to each well. The co-stimulation response was continuously monitored for an additional one hour. All studies were carried out at controlled temperature (28° C.) and with three replicates for each measurement, unless specifically mentioned. The assay coefficient of variation was found to be <10%. All data analysis was carried out using either Microsoft Excel, or Prism software (Graph Pad).

EXAMPLES

The following examples serve to more fully describe the manner of using the disclosure, as well as to further illustrate and demonstrate specific examples of best modes contemplated for carrying out various aspects of the disclosure.

These examples do not limit the scope of the disclosure, but rather are presented for illustrative purposes.

Example 1

Optical responses of quiescent A431 cells upon c-stimulation with both SFFLR-amide and epinephrine, or both bradykinin and epinephrine The notion of compartmentalization in which unique changes in second messenger levels occur in both time and space was established with the advent of high resolution single-cell imaging systems in combination with fluorescent probes. It is widely believed that GPCR signaling proceeds through a series of highly regulated spatial and temporal events besides the production and regulations of second messengers such as $Ca^{2+}$ and cAMP. However, such "tunneling" or "channeling" of the series of signaling events through a receptor has not been previously demonstrated or established. The label-free optical biosensors enable the measurement of an integrated cellular response relating to ligand-induced dynamic mass redistribution in cells within the detection zone of the biosensor, offering a novel readout for receptor biology and ligand pharmacology. Here the biosensor cellular assays were used to investigate the optical response of quiescent A431 cells in response to co-stimulation with SFLLR-amide and epinephrine. SFFLR-amide mediated signaling through endogenous $G_q$-coupled protease activated receptors (see Fang, Y. and Ferrie, A. M. "Optical biosensor differentiates signaling of endogenous PAR1 and PAR2 in A431 cells," BMC Cell Biol., 2007, 8, 24), whereas epinephrine mediated signaling is through endogenous $G_s$-coupled β2-adrenergic receptor (β2AR) (see Fang, Y. et al., "Non-invasive optical biosensor for assaying endogenous G protein-coupled receptors in adherent cells," Journal of Pharmacological & Toxicological Methods, 2007, 55, 314-322).

Figure 2B:
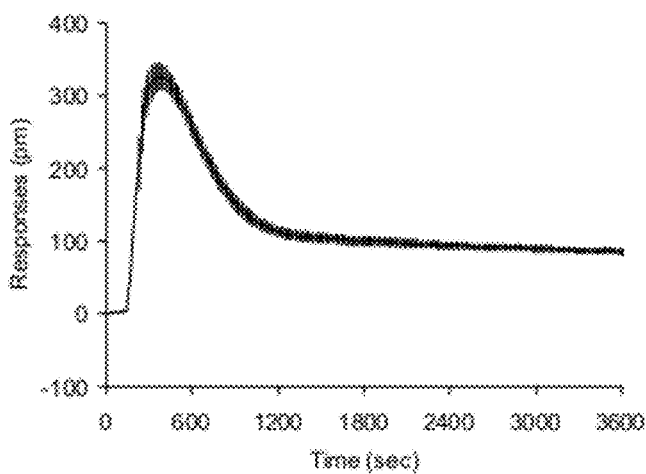
Figure 2C:
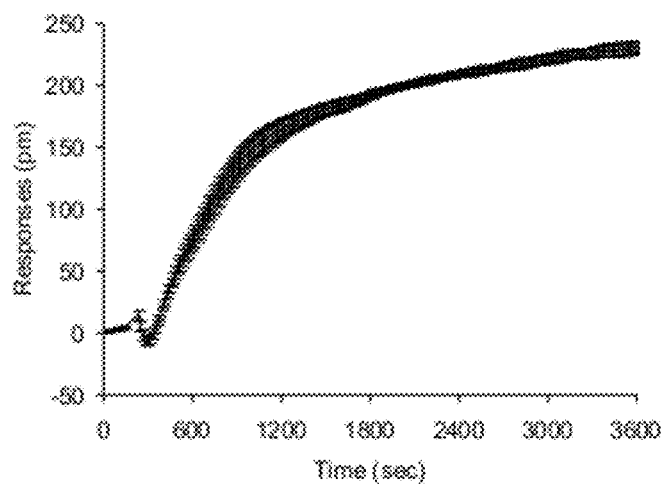
Figure 2D:
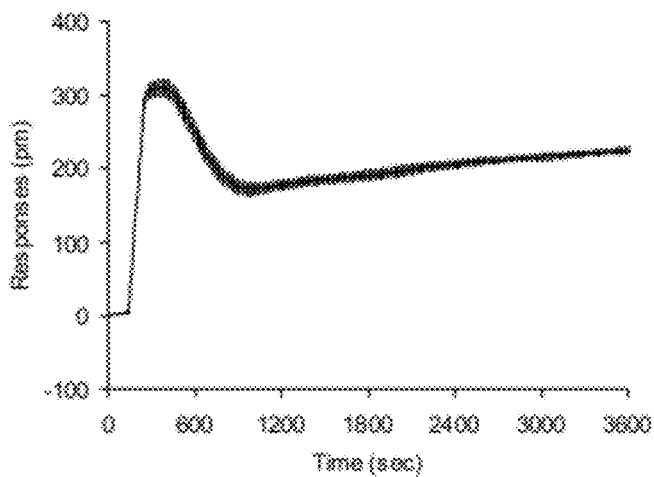

FIG. 2 provide examples of RWG biosensor-based cell assays against two classes of G protein-coupled receptors. FIG. 2a shows $G_q$-coupled receptor (protease activated receptor subtype 1, $PAR_1$) (210) and $G_s$-coupled receptor (β2 adrenergic receptor, β2AR) (220) in A431 cells. A431 cells endogenously express both $PAR_1$ and β2AR. SFLLR-amide (215) is a $PAR_1$-specific agonist, while epinephrine (225) is a β2AR-specific agonist. FIG. 2b shows that stimulation of A431 cells with, for example, 1 micromolar SFLLR-amide leads to a $G_q$-type DMR signal. FIG. 2c shows that stimulation of A431 cells with, for example, 2 nanomolar epinephrine leads to a $G_s$-type DMR signal. This is consistent with the known signaling pathways mediated through each receptor individually, i.e., $PAR_1$ activation leads to a $G_q$ pathway, while β2AR activation leads to a $G_s$ pathway. FIG. 2d shows that co-stimulation of A431 cells with SFLLR-amide (1 micromolar) and epinephrine (2 nanomolar) leads to an optical signature that appears to be the sum of the optical signatures induced by SFLLR-amide and epinephrine individually. In FIGS. 2b, 2c and 2d, the error bar at each time point was also included. One possible explanation is that distinct classes of GPCRs can mediate signaling through distinct routes (e.g., "channeling" or "tunneling"), and the cells can respond synergistically to co-stimulation with two agonists targeting two different receptors.

Figure 3A:
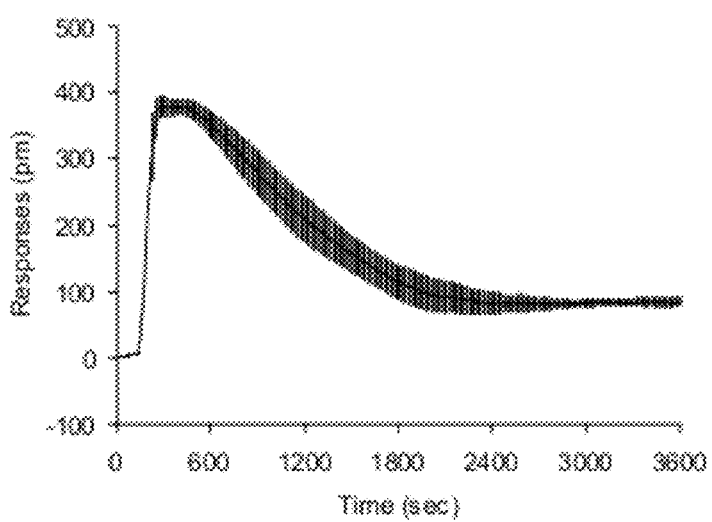
FIGS. 3A-3C show another exemplary RWG biosensor-based cell assay against two classes of G protein-coupled receptors, in embodiments of the disclosure.
Figure 3B:
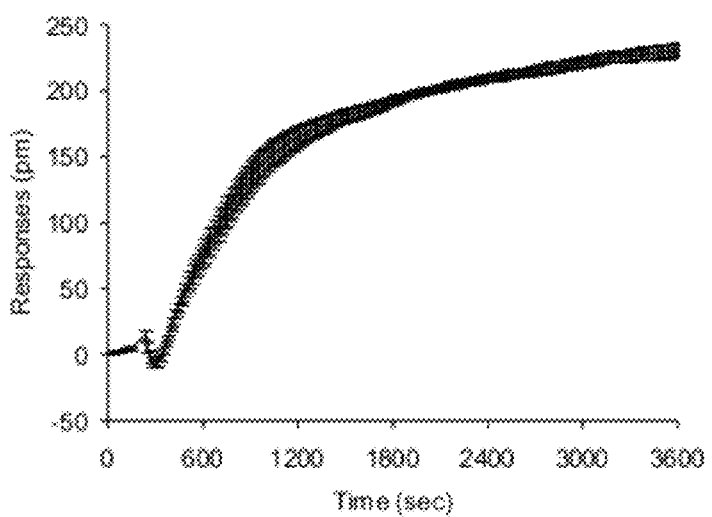
Figure 3C:
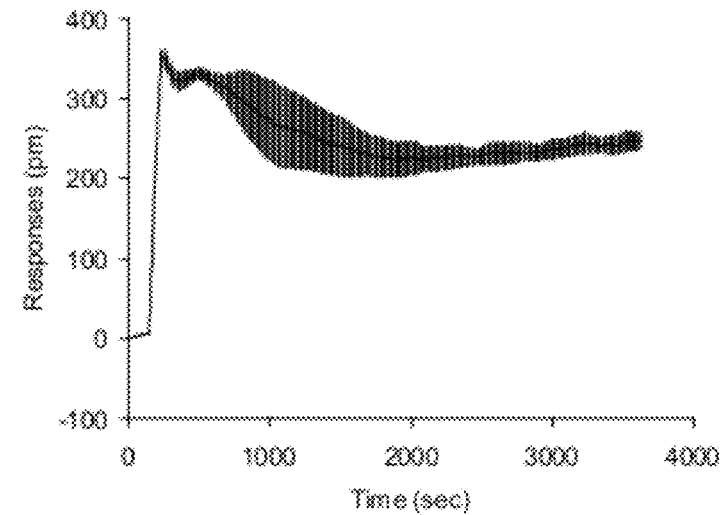

Similar results were observed for co-stimulation of A431 cells with bradykinin and epinephrine. FIG. 3 provides an example of RWG biosensor-based cell assays against two classes of G protein-coupled receptors: $G_q$-coupled receptor (bradykinin B2 receptor) and $G_s$-coupled receptor (β2 adrenergic receptor, β2AR) in A431 cells. A431 cells endogenously express both B2 receptor and β2AR. Bradykinin is a B2-specific agonist, while epinephrine is a β2AR-specific agonist. FIG. 3a shows that stimulation of A431 cells with 16 nanomolar bradykinin leads to a $G_q$-type DMR signal. FIG. 3b shows that stimulation of A431 cells with 2 nanomolar epinephrine leads to a $G_s$-type DMR signal. This is consistent with the known signaling pathways mediated through each receptor, i.e., B2 activation leads primarily to a $G_q$ pathway, whereas P2AR activation leads to a $G_s$ pathway. FIG. 3c shows that co-stimulation of A431 cells with bradykinin (2 nanomolar) and epinephrine (2 nanomolar) leads to an optical signature that closely resembles the sum of the optical signatures induced by bradykinin and epinephrine individually. In FIGS. 3a, 3b and 3c, the error bar at each time point was also included to show that the kinetic response is highly reproducible.

Example 2

Figure 4:
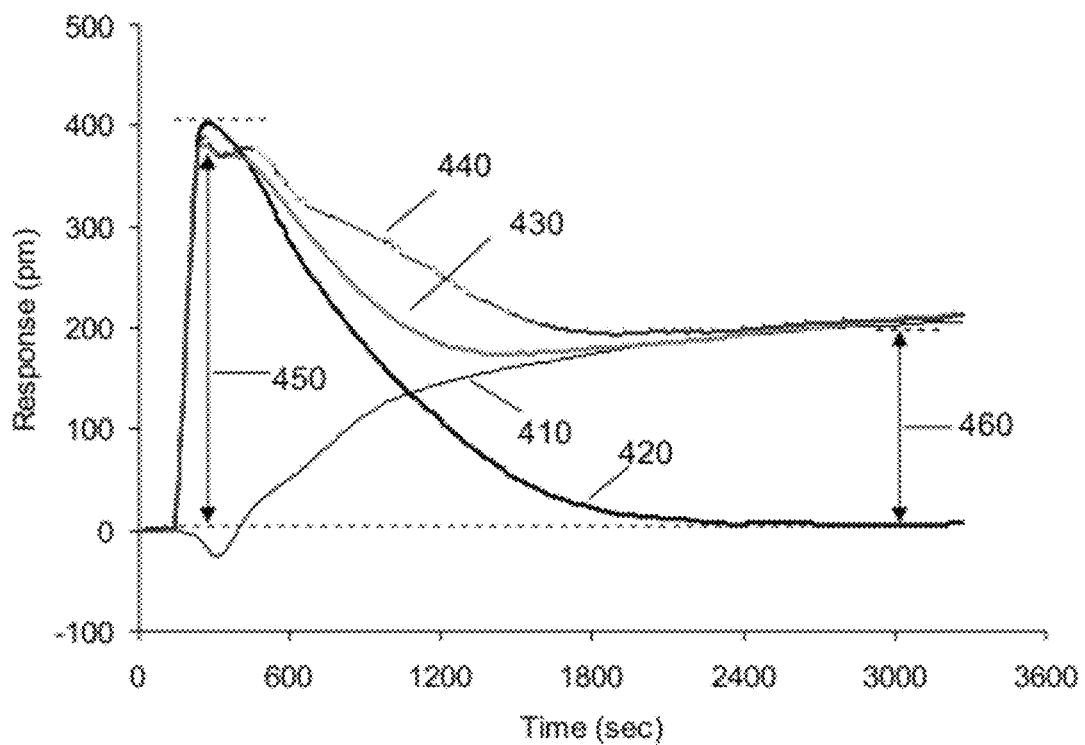
FIG. 4 shows results of an exemplary duplexed and target-specific screen using an RWG biosensor, in embodiments of the disclosure.
Figure 5A:
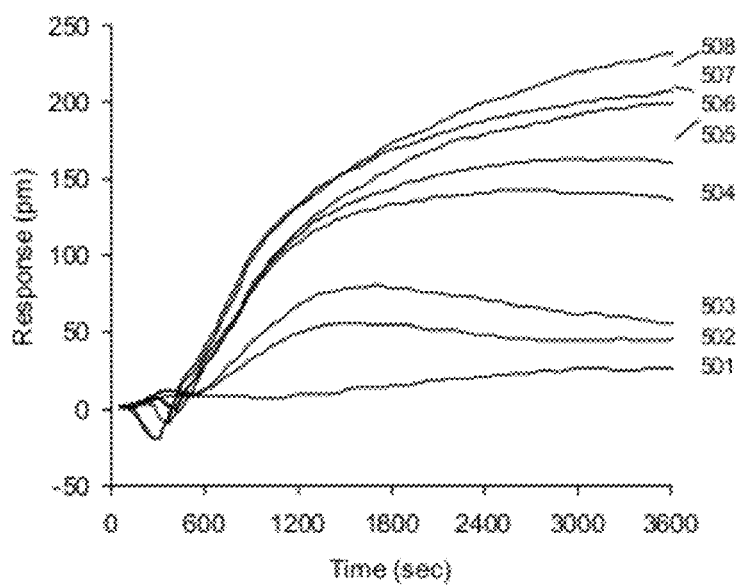
FIGS. 5A-5C show results of exemplary optical biosensor cellular assays for two endogenous receptors in A431 cells—β2-adrenergic receptor and histamine H1 receptor, in embodiments of the disclosure.
Figure 5B:
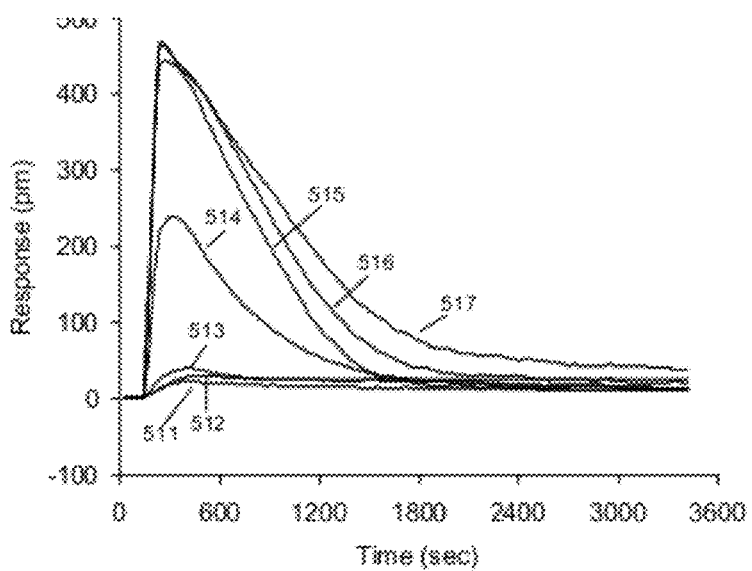
Figure 5C:
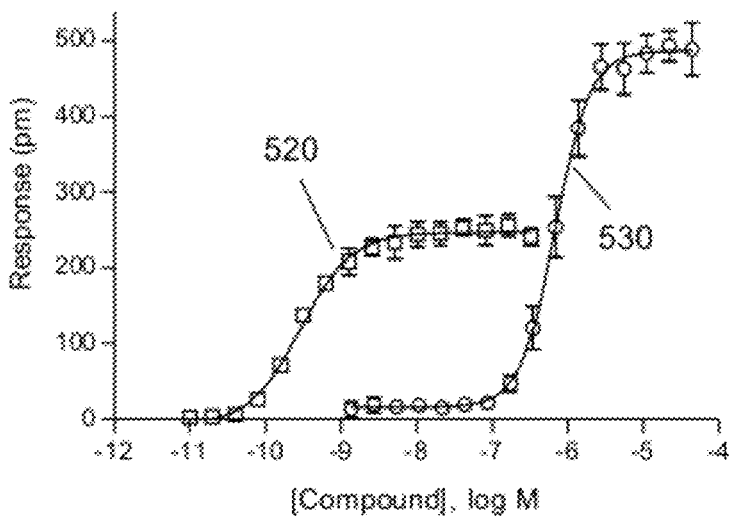

Optical responses of quiescent A431 cells upon co-stimulation with epinephrine and histamine A431 endogenously expresses large numbers of the β$_2$AR, but neither β$_1$ nor β$_3$-ARs. Epinephrine mediated a biphasic $G_s$-type DMR response in quiescent A431 cells (410) (FIG. 4). The DMR signal consists of a small decreased signal (i.e., N-DMR) with a short duration, followed by an increased signal (i.e., P-DMR) to an elevated level. The epinephrine response was dose-dependent and saturable (520), leading to an apparent $EC_{50}$ of 0.08±0.03 nM and a Hill slope of 0.95 (n=10) (FIG. 5a and FIG. 5c). In FIG. 5a, cells were stimulated with epinephrine at different doses (501: 0.01 nanomolar (nM); 502: 0.02 nM; 503: 0.04 nM; 504: 0.08 nM; 505: 0.16 nM; 506: 0.64 nM; 507: 2.56 nM; 508: 10.25 nM), whose real time kinetic responses were recorded. The β-blocker propranolol dose-dependently attenuated the epinephrine response (data not shown), suggesting that the epinephrine response is β$_2$AR-specific.

A431 also endogenously expresses histamine receptor subtype 1 ($H_1R$). The stimulation of quiescent A431 cells with histamine led to a dose-dependent and saturable $G_q$-type optical signal, which consists of an initial P-DMR and a subsequent N-DMR (420) (FIG. 4). The histamine responses were also saturable (FIG. 5b). In FIG. 5b, cells were stimulated with histamine at different doses: 511: 2.7 nM; 512: 43.5 nM; 513: 174 nM; 514: 696 nM; 515: 2,784 nM; 516: 11,138 nM; 517: 445,506 nM. The saturation curve (530), as plotted as the P-DMR amplitude as a function of histamine concentration, appeared to fit well with sigmoidal non-linear regression with variable slope, leading to an apparent $EC_{50}$ of 687±34 nM (n=6) and a Hill coefficient of 1.87 (FIG. 5c). The very steep activation curve observed suggests that there is positive cooperativity of the receptor through unknown mechanism(s). The pretreatment of A431 with $H_1$ specific antagonists (±)-brompheniramine, (±)chlorpheniramine, clemizole, clemastine, diphenhydramine, or triprolidine, each at 1 μM, completely inhibited the DMR signal induced by 1 μM histamine. Conversely, the $H_2$ antagonists SKF91488 and ranitidine at 1 μM did not have obvious impact on the histamine response, nor did $H_3$-specific antagonist thioperamide. These results suggest that the histamine response is largely $H_1R$-specific.

Compartmentalized signaling in which unique changes in second messenger levels occur in both time and space has been established and is known to be central in GPCR signaling. Since the DMR signal is a global measure of receptor signaling at least in terms of mass redistribution within the sensing volume of the biosensor, the co-activation of two receptors coupled to distinct classes of G proteins could lead to a DMR signal that is largely a sum of the two DMR signals mediated through the activation of each receptor. To test this hypothesis, quiescent A431 cells were stimulated with epinephrine and histamine individually or together. Results showed that indeed stimulation of quiescent A431 cells with 1 μM histamine and 2 nM epinephrine led to a unique DMR signal (430) that closely resembles the sum (440) of the two DMR signals obtained individually (FIG. 4). Because of its simply additive nature, the early P-DMR event is referred to the histamine response (450), and the retarded P-DMR event is the epinephrine response (460). Together with examples shown above, these results represents the first evidence that distinct classes of GPCRs can mediate signaling mostly independently, strongly suggesting that spatial and temporal compartmentalization of signaling cascades is central to GPCR signaling. Most of cellular events downstream of a receptor signaling occur as "tunneling" or "channeling".

Figure 6A:
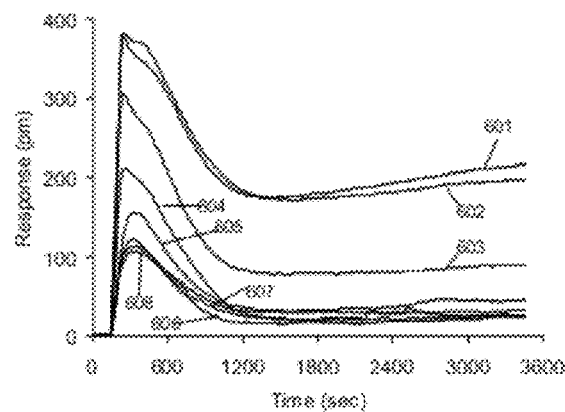
FIGS. 6A-6D show results of an exemplary duplexed and target-specific screen using an RWG biosensor, in embodiments of this disclosure.
Figure 6B:
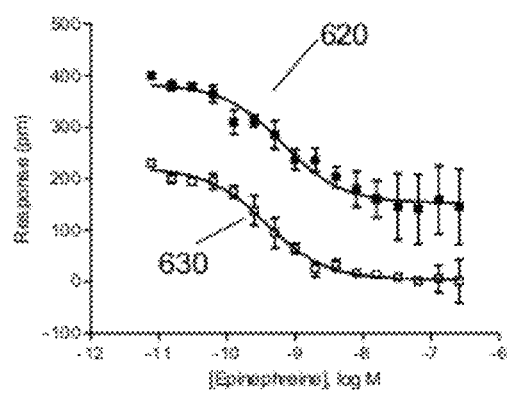
Figure 6C:
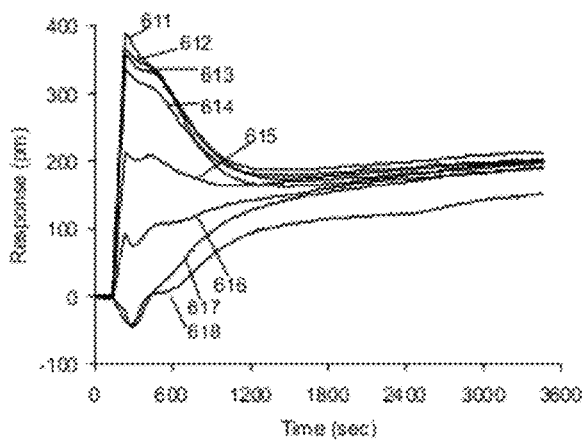
Figure 6D:
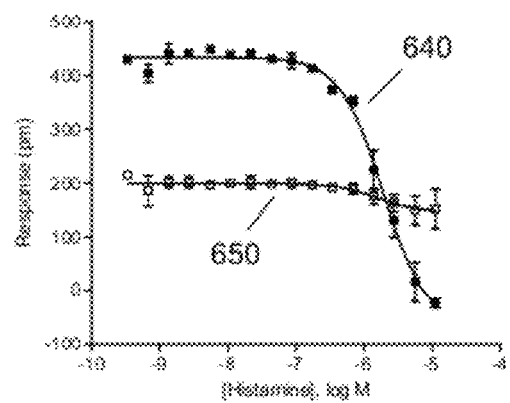

Interestingly, the co-stimulation DMR signal is not a simple addition of the two individual DMR signals—its initial P-DMR was largely identical to the calculated signal, whereas its second decaying phase exhibited faster kinetics and bigger amplitude than the calculated signal. Although not bound by theory this may be due to the crosstalk of the histamine mediated signaling with the epinephrine mediated signaling. It is known that the activation of $G_q$-coupled receptors leads to the regulation of adenylate cyclases in cAMP microdomains. To test this possibility, a desensitization assay was used. Here A431 cells were first pre-treated with either epinephrine or histamine at different doses, followed by co-stimulation with the cocktail solution containing 2 nM epinephrine and 1 μM histamine. Results showed that epinephrine dose-dependently attenuated both the histamine response and the epinephrine response (FIG. 6a), with almost identical $IC_{50}$ (0.66±0.20 nM, and 0.38±0.09 nM (n=4), respectively) (FIG. 6b). In FIG. 6a, the cells were pretreated with epinephrine at different doses (601: 0.01 nM; 602: 0.03 nM; 603: 0.13 nM; 604: 0.50 nM; 605: 2 nM; 606: 8 nM; 607: 32 nM; 608: 256 nM), followed by co-stimulation with 1,000 nM histamine and 2 nM epinephrine. Only real time co-stimulation-induced DMR signal were recorded and shown in FIG. 6a. In FIG. 6b, both the epinephrine response (630) and the histamine response (620) were plotted as the function of epinephrine concentrations used for the cell pretreatment. Epinephrine at high doses completely inhibited the later epinephrine response, but only partially attenuated the early histamine response. Conversely, the pretreatment of cells with histamine completely inhibited the histamine response with an apparent $IC_{50}$ of 1.6±0.4 μM and a Hill slope of 1.4 (n=4), but slightly attenuated the epinephrine response (FIG. 6c and FIG. 6d). In FIG. 6c, the cells were pretreated with histamine at different doses: 611: 2.7 nM; 612: 10.9 nM; 613: 43.5 nM; 614: 174 nM; 615: 696 nM; 616: 2,784 nM; 617: 11,138 nM; 618: 44,550 nM), followed by co-stimulation with 1,000 nM histamine and 2 nM epinephrine. Only real time co-stimulation-induced DMR signal were recorded and shown in FIG. 6c. In FIG. 6d, both the epinephrine response (650) and the histamine response (640) were plotted as the function of epinephrine concentrations used for the cell pretreatment. These results suggest that the $G_q$-coupled receptor $H_1R$ indeed cross-talks with $G_s$-coupled receptor $\beta_2AR$, possibly through cAMP-PKA pathway. Nonetheless, these results demonstrate a dual receptor-specific screening method using the label-free biosensor cellular assays.

Example 3

Figure 7B:
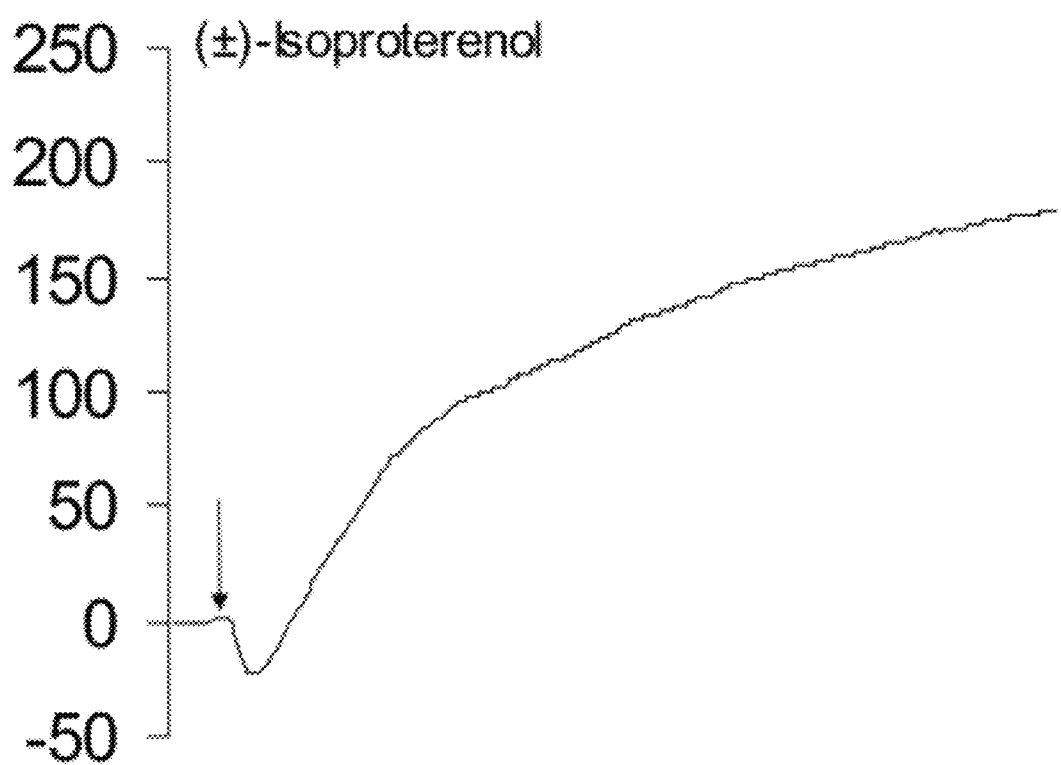
Figure 7C:
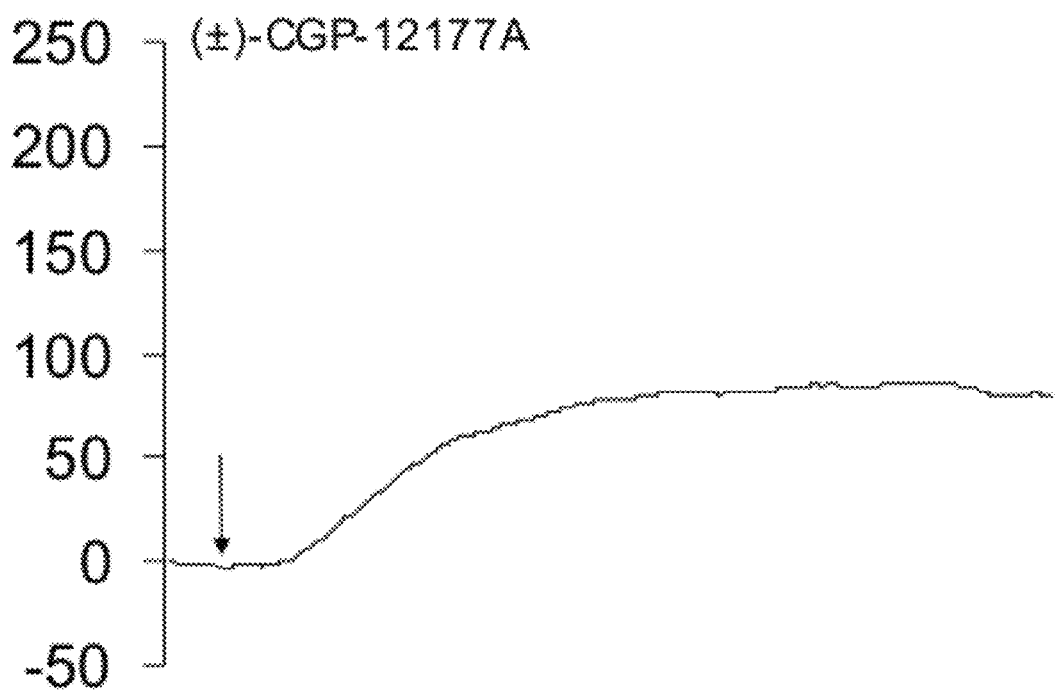
Figure 7D:
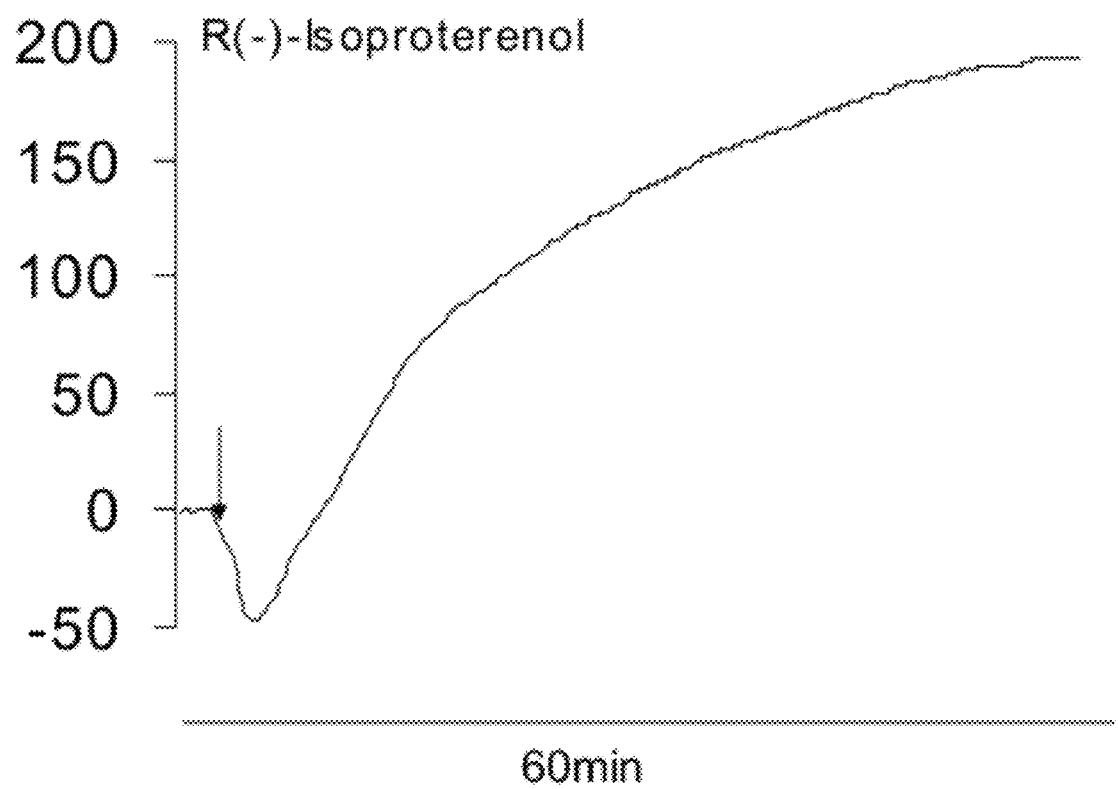
Figure 7E:
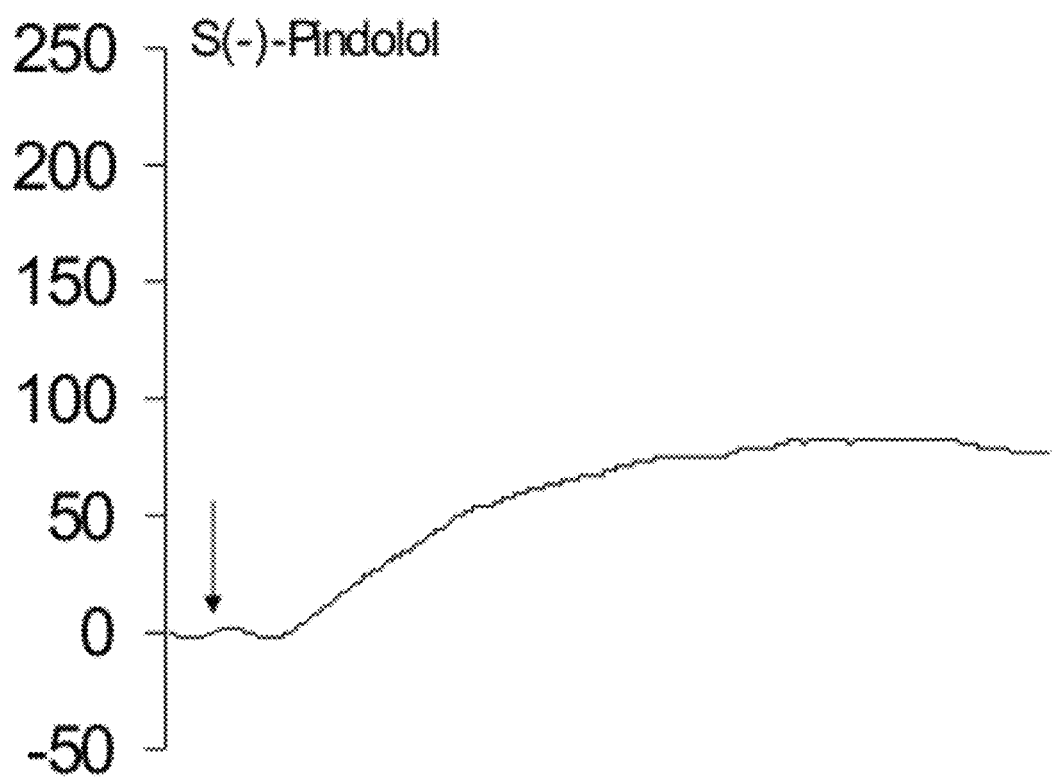
Figure 7F:
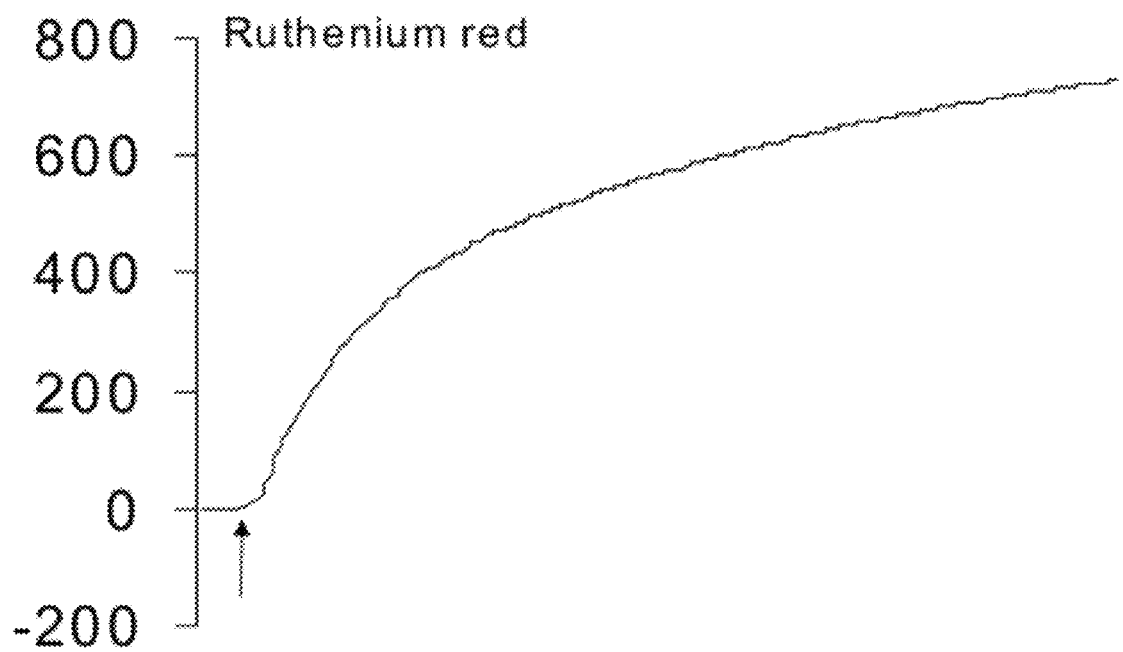

Optical biosensor cellular assays for agonist screening using LOPAC library acting on A431 cells—The Sigma-Aldrich LOPAC 1280™ library of compounds includes 1,280 bioactive small organic molecules against all major target classes including several GPCRs, and was chosen to validate screening using the biosensor cellular assays. Since a ligand-induced DMR signal is an integrated response and many ligands often exhibit cross-activity to more than one receptor in the cells, the library members were diluted in 1×HBSS containing 0.1% DMSO to achieve 1 microM final concentration for screening to minimize the off-target effect. Furthermore, a ligand-induced DMR is a real time kinetic response containing many useful parameters (e.g., phases, amplitudes and kinetics) for analyzing ligand pharmacology. The LOPAC library was used to screen agonists for endogenous receptors in A431 cells using real time kinetic measurements. FIG. 7 summarizes some representative classes of DMR signals that were obtained with the library using the method. Histamine led to a biphasic $G_q$-type DMR signal (FIG. 7a). The β2AR full agonists (±)isoproterenol and R(−)isoproterenol led to a typical $G_s$-type DMR signal (FIG. 7b and FIG. 7d, respectively). The two $\beta_2AR$ partial agonists (±)CGP12177 and S(−)pindolol led to a $G_s$-like DMR which only consists of the prolonged P-DMR event without the initial N-DMR event (FIG. 7c and FIG. 7e). Ruthemium red, an inhibitor of mitochondrial $Ca^{2+}$ uniporter and VR1 vanilloid receptor-coupled ion channel, also led to a $G_s$-like DMR signal but with much larger amplitude (FIG. 7f). Like many compounds in the library, the potent $H_1$ antagonist triprolidine did not lead to any significant DMR signal (referred to as a net zero-DMR) (data not shown).

Based on the kinetic profiles of both the epinephrine response and the histamine response, four types of end-point measurements were chosen to determine the response of compounds in the library. First, the response in terms of wavelength shift between before and 2 min after stimulation was calculated. Results showed that using this end-point measurement, only one hit, histamine, was identified from the library (data not shown). Since the initial N-DMR event in the epinephrine was relatively small, such end-point measurement appeared to be insufficiently robust to identify $G_s$-coupled receptor agonists. Conversely, since the initial P-DMR event in the histamine response was quite large, such end-point measurement was well-suited for identifying agonists for $G_q$-coupled receptors.

Second, the responses in terms of wavelength shift between before and 50 min after stimulation were calculated. Results showed that this end-point measurement was well-suited for identifying agonists for $G_s$-coupled receptors (data not shown). However, it fails to identify agonists for $G_q$-coupled receptors, since the $G_q$-type DMR consists of an initial rapid P-DMR and a subsequent slow N-DMR that almost decays back to the initial baseline (FIG. 4 and FIG. 5b).

Figure 8:
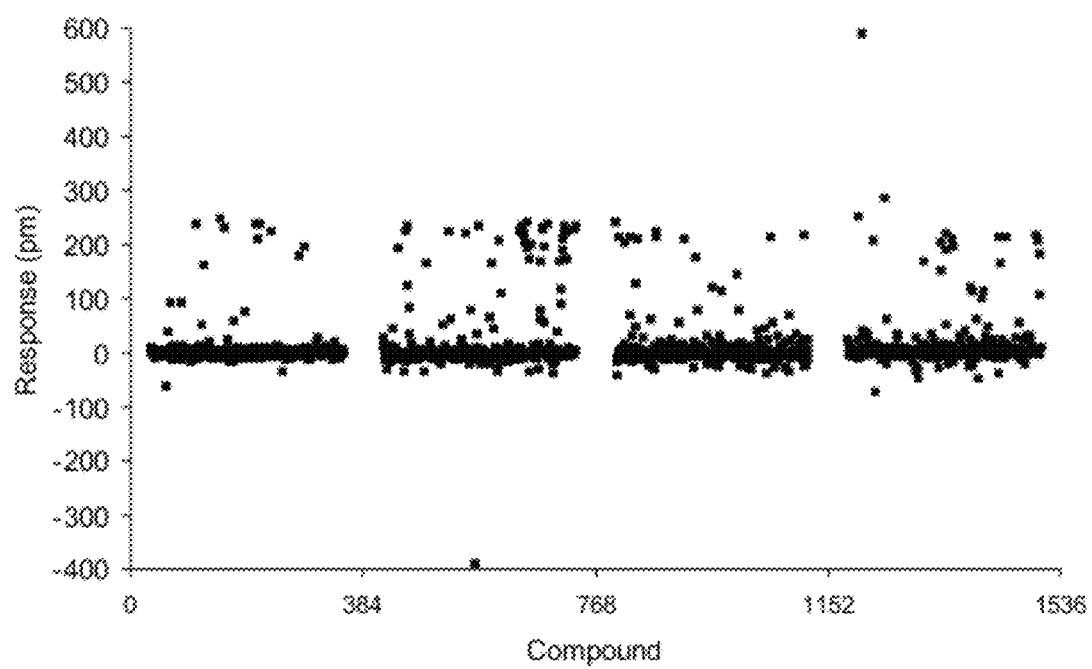
FIG. 8 shows results of an exemplary compound library screening for agonists using biosensor cellular assays, in embodiments of this disclosure.

Third, the responses in terms of wavelength shift between 2 min and 50 min after stimulation were calculated. The difference in resonant wavelength between the two time points was plotted as a function of compounds (FIG. 8). Results showed that such two time point measurement is sufficient and robust to identify agonists in the library for both $G_q$-coupled receptors and $G_s$-coupled receptors. Similar hits were selected using a three point measurement, i.e., 2 min before and 50 min after stimulation (data not shown). Thus, the responses measured with the wavelength shift from 2 min to 50 min after stimulation were used for selecting hits for both H1R and $\beta_2AR$. An agonist for H1R would lead to a large negative response, whereas a $\beta_2AR$ agonist would lead to a positive response.

As shown in FIG. 8, there was only one hit for $G_q$-coupled H1R. Histamine led to a large negative response. In the LOPAC, histamine is the only broad spectrum histamine receptor agonist, although there are two H3R specific agonists R(−)-α-methyl-histamine and imetit. The two H3R agonists at 1 μM did not lead to any obvious DMR signal. Beside histamine receptor agonists, P2Y agonists of 1 μM in the library also did not lead to any apparent or specific DMR signal, although the A431 endogenously expresses $G_q$-coupled P2Y receptors. Although not limited by theory this was probably due to the low potency of these agonists to activate P2Y receptors.

Conversely, there were many hits that lead to positive responses having distinct amplitudes. Based on the epinephrine positive controls which lead to a response of 225±18 pm (n=64), hits that led to a response from 170 to 280 pm were considered as full or strong partial agonists. Results showed that 63 hits acted as full or strong partial agonists—12 adenosine receptor agonists, 27 adrenoceptor agonists, and 7 dopamine receptor agonists. In addition, hits that lead to a response from 40 to 170 were considered as partial or weak partial agonists. Results showed that 51 hits fell into this category, including 6 adenosine agonists, 6 adrenoceptor agonists, and 5 dopamine agonists. This high positive hit rate reflects the fact that A431 also endogenously expresses adenosine receptors, whose activation also leads to an epinephrine-like DMR response. Furthermore, many dopamine agonists are known to activate the β2AR. Except for two low potency beta-adrenoceptor agonists, (±)-ephedrine and amiodarone, all other beta-adrenoceptor agonists in the library were correctly identified. Such low false negative rate demonstrates in-part the viability of the disclosed biosensor cellular assay method for screening ligands against endogenous GPCRs.

Example 4

Figure 9A:
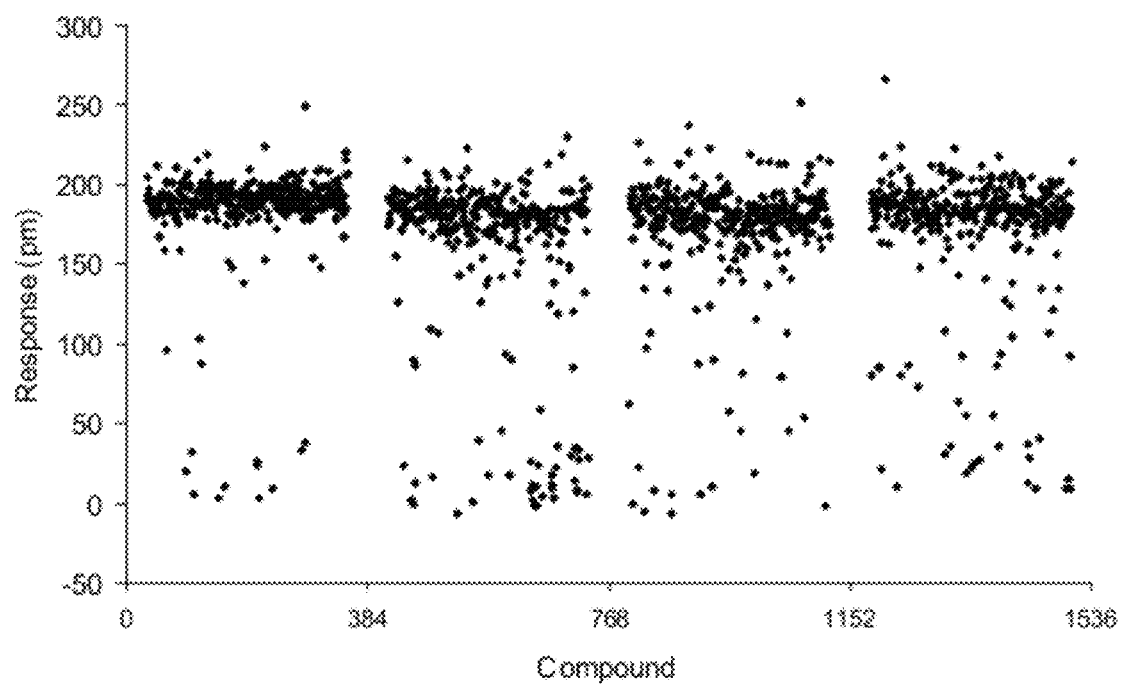
FIGS. 9A-9B show results of an exemplary compound library screening for antagonists using biosensor cellular assays, in embodiments of this disclosure.
Figure 9B:
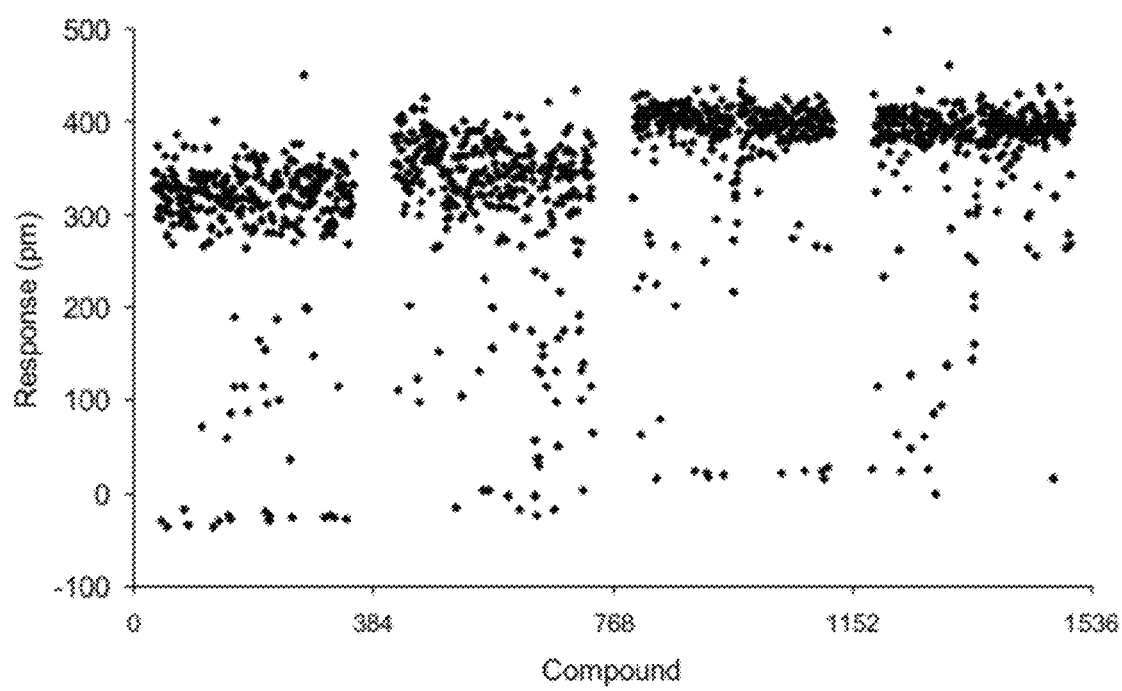

Dual receptor-specific antagonist screening with the biosensor cellular assays Since the co-stimulation of A431 cells with histamine and epinephrine led to a DMR signal that contains characteristics from both the histamine- and epinephrine-mediated signaling, the possibility of dual receptor-specific screening with the biosensor cellular assays was examined. This assay proceeds with the initial agonist screening with the biosensor for one hour, followed by a co-stimulation with histamine and epinephrine. The impacts of compounds in the library on both the histamine response and the epinephrine were examined based on their corresponding DMR amplitudes (FIG. 9). For the epinephrine response, there were 77 hits that caused complete inhibition (20±30 pm), 57 partial inhibitors (90±40 pm), and 1,146 non-inhibitors (190±60 pm). For the histamine response, there were 51 hits that caused complete inhibition (15±50 pm), 79 partial inhibitors (165±100 pm), and 1,160 non-inhibitors (370±110 pm).

Correlation analysis between the initial agonist screening and the subsequent antagonist screening provides further clarification about the action of positive hits acting on H1R or β2AR. Histamine led to a $G_q$-like DMR signal and also caused the complete desensitization of cells to histamine but not to epinephrine. All known H1R antagonists in the library did not lead to any DMR signal. These ligands included (±)-brompheniramine, (±)-chlorpheniramine, (+)-brompheniramine, (+)-chlorpheniramine, clemizole, clemastine, diphenhydramine, fexofenadine, doxylamine, methapyrilene, promethazine, pyrilamine, terfenadine, ketotifen, loratadine, pheniramine, and triprolidine. Except for ketotifen, loratadine and pheniramine that at 1 microM only caused partial inhibition of the histamine response, all other H1R-specific antagonists completely or almost completely attenuated the histamine response. Conversely, neither H2R- nor H3R-specific antagonists in the library caused any significant inhibition on the histamine response, suggesting that the histamine response is largely H1R-specific. Interestingly, the two H2R antagonists famotidine and SKF95282 led to a DMR that was similar to pindolol, and also caused partial desensitization of cells to epinephrine but not to histamine, suggesting that the two ligands crosstalk to endogenous $G_s$-coupled receptors in A431. Furthermore, several adrenoceptor uptake/reuptake inhibitors almost completely inhibited the histamine response, but had little effect on the epinephrine response. They were protriptyline, phenoxybenzamine, amoxapine, maprotiline, desipramine, nortriptyline, amitriptyline, and doxepin.

The adrenergic receptor ligands that led to significant DMR signals also caused desensitization of cells responding to epinephrine; and the desensitization was largely correlated with the amplitude of a ligand-induced P-DMR event. However, these ligands greatly differ in their ability to attenuate the histamine response. Conversely, for adrenergic receptor ligands that did not result in any apparent DMR signals, only 10 of these antagonists inhibited or partially attenuated the epinephrine response. These were alprenolol, betaxolol, S(−)-timolol, (S)-(−)-propafenone, (S)-propranolol, (±)-metoprolol, SR 59230A, (±)-propranolol, ICI 118,551, and (±)-Sotalol. The ten beta blockers had little impact on the histamine response.

Evidence accumulated in recent years suggest that receptors and their downstream signaling pathways do not work in isolation. They are connected via many fold interactions (cross-talk) and associated in signaling networks. Distinct receptors can cross-talk at multiple levels. This cross-talk can occur through interaction of intracellular signal transduction pathways, phosphorylation of receptors and regulatory proteins by kinases, or effects on intracellular calcium release. This cross-talk ensures the exchange of information between the individual signaling pathways and provides the molecular basis for their cooperation. Thus, stimulation of a particular receptor leads to activation of a signaling pathway that can subsequently interact with those activated by other receptors. There has been growing recognition and acceptance that physical interaction between cell surface receptors may provide a useful method of accomplishing receptor cross-talk investigations. Receptor cross-talk represents a method of fine-tuning the control of cellular function and is relevant to understanding disease and response to therapeutic agents that interact with cell-surface receptors. Cross-talk between different G protein-coupled receptors (GPCRs) is well known and results mostly in synergistic effects and the amplification of cellular responses. Using the disclosed biosensor cellular assays, we have found that histamine slightly attenuated the epinephrine response, whereas epinephrine partially attenuated the histamine response, both in a dose-dependent manner. It is known that the cAMP-PKA pathway plays a central role in the integration of signaling mediated through distinct classes of GPCRs; and the ubiquitous second messenger $Ca^{2+}$ can regulate many adenylyl cyclases, and such regulation provides an overarching mechanism for integrating the activities of these two major signaling systems. Furthermore, the co-stimulation DMR signal is largely, but not simply an additive function of the two individual DMR signals, but also indicates that there may be cross-talk between signaling mediated through the two receptors. In addition, many adenosine receptor agonists in the library also caused complete attenuation of the epinephrine response. This is consistent with the well-established heterologous desensitization in which distinct $G_s$-coupled receptors can cause cross-desensitization through the cAMP-PKA pathway.

The disclosed biosensor cellular assays can be used for multiplexed screening in several respects. First, the biosensor cellular assays are multiplexing in nature for agonist screening. The biosensor is capable of monitoring endogenous receptor activation, leading to high-information and physiologically relevant measures of a receptor-ligand pair. These assays do not require prior knowledge of cell signaling, and are pathway-unbiased. However, the optical responses recorded are pathway-sensitive, and do reflect the complexity of receptor signaling. A431 cells endogenously express adenosine receptors, and β2AR and histamine receptors, whose ligands are also presented in the LOPAC library. In this agonist screening, ligands at 1 µM were used to stimulate the cells. Results showed that ligands that led to significant DMR signals were primarily from three families of compounds: ligands for adrenergic receptors; adenosine receptors; and histamine receptors. Some dopamine receptor ligands that are known to be able to activate the β2AR also led to an epinephrine-like response, and were identified as hits for the β2AR. However, four of the P2Y agonists in the library did not lead to any significant DMR signals, probably due to their low potencies (data not shown). Since A431 cells expresses other receptors (e.g., protease activated receptors, bradykinin B2 receptor, and epidermal growth factor receptor) whose activation was also detectable with the biosensor cellular assays, ligands for these receptors if presented in the library would also be identified as hits.

The disclosed biosensor cellular assay methods can also be multiplexing for antagonist screening. Besides desensitization upon repeated stimulation with agonists that target the same receptor, in many cases cells tend to loss their responsiveness through heterologous desensitization. Thus, an agonist for another receptor (e.g., adenosine receptors) could act as an antagonist for the target receptor (e.g., β2AR). Furthermore, since the biosensor cellular assays measure an integrated DMR response, an agonist for a receptor (e.g., β2AR) could partially attenuate the response of the target receptor which even mediates signaling through distinct pathway (e.g., a $G_q$-coupled H1R). In addition, pathway modulators can also act as an antagonist for the target receptor.

A ligand-induced DMR signal, as measured using the label-free optical biosensor, can be an integrated response and consists of contributions of many cellular events downstream of the receptor activation, particularly those leading to significant mass redistribution within the sensing volume of the biosensor. Contributions from these events mediated through a receptor that make the biosensor cellular assays so valuable, however, also render the optical signal obtained "non-specific" relative to conventional cellular assays. Many ligands often exhibit cross-activity to more than one receptor in a cell type or cell system. Furthermore, many GPCR ligands can often induce an operative bias to activate specific portions of cell signaling through a receptor, and thus exhibit ligand-directed functional selectivity. Therefore, caution should be exercised when analyzing GPCR ligand pharmacology and screening ligands for the target receptors using the biosensor cellular assays. To achieve target-specific screening, several approaches can be applied. For a given cell or cell system, receptor panning should be performed to determine how many receptors can be detected using the biosensor cellular assays. Then receptor biology and ligand pharmacology should be studied to determine the potential for interference of a receptor with the target receptor, and to systematically evaluate the signaling potentials of the target receptor. If one or more endogenous receptors interfere with the target receptor, a cocktail solution containing antagonists that block the activity of these receptors can be used to minimize false positives for the target receptor. Alternatively, a cell engineering approach can also be used to either boost the target-specific DMR signal, or to suppress the signal mediated through receptors other than the target. A counter screen between a parental cell line and an engineered cell line having or not having the target receptor can be performed to establish positive hits for the target receptor.

The disclosure has been described with reference to various specific embodiments and techniques. However, it should be understood that many variations and modifications are possible while remaining within the spirit and scope of the disclosuure.

REFERENCES

1. Fang, Y., et. al., *J. Biophys. J* 91, 1925-1940 (2006).
2. Fang, Y., et. al., *Anal. Chem.* 77, 5720-5725 (2005).
3. Fang, Y., et. al., *FEBS Lett.* 579, 6365-6374 (2005).
4. Fang, Y., et. al., *J. Pharmacol Toxicol. Methods* 55, 314-322 (2007).
5. Fang, Y., *Assays and Drug development Technologies,* 4, 583-595 (2006).

What is claimed is:

1. A label-free duplex screening method comprising:
   providing an optical biosensor having a single type of live-cell immobilized on a surface of the biosensor, the biosensor being situated in a well of a microtiter plate, and the live-cell having at least two different targets;
   contacting the immobilized cell with a ligand candidate;
   contacting the ligand candidate-treated cell with a mixture containing two markers; and
   determining the effect of the ligand candidate on the marker mixture-induced biosensor output.

2. The method of claim 1 wherein the at least two different targets comprise a first target and a second target that are distinguishable from each other by the biosensor.

3. The method of claim 1 wherein each of the markers selectively modulates the activity of one of the different targets.

4. The method of claim 1 wherein the ligand candidate comprises at least one of a chemical compound, a biological molecule, a peptide, a protein, a biological sample, a drug candidate small molecule, a drug candidate biological molecule, or a drug candidate small molecule-biological conjugate.

5. The method of claim 1 wherein the target comprises at least one of a receptor, or a cellular protein.

6. The method of claim 5 wherein the receptor comprises at least one of a $G_q$-coupled receptor, a $G_s$-coupled receptor, a $G_i$-coupled receptor, a $G_{12/13}$-coupled receptor, a receptor tyrosine kinase, an ion channel, a sodium-proton exchanger, an integrin receptor, or a transporter.

7. The method of claim 5 wherein the cellular protein comprises at least one of a cellular enzyme, a cellular kinase, or a cellular structural protein.

8. The method of claim 1 wherein the marker comprises at least one of an agonist, a partial agonist, or an inverse agonist, the agonist being capable of activating a target and producing a detectable biosensor output signal.

9. The method of claim 1 wherein the marker comprises at least one of an inhibitor, or an antibody, the marker being capable of activating a target and producing a detectable biosensor output signal.

10. The method of claim 1 wherein each of the markers specifically modulates the activity of a distinct target.

11. The method of claim 10 wherein the targets comprise at least one of a pair of $G_q$-coupled receptors, a pair of a $G_q$-coupled receptor and a $G_s$-coupled receptor, a pair of a $G_i$-coupled receptor and a $G_s$-coupled receptor, a pair of a G protein-coupled receptor and a receptor-tyrosine kinase, or a pair of a receptor and a cellular protein.

12. The method of claim 1 wherein the effect of the ligand candidate on the biosensor output comprises modulation of the marker-induced signal responses.

13. The method of claim 12 wherein the modulation comprises a change in signal amplitude, dynamics, kinetics, or a combination thereof.

* * * * *